(12) United States Patent
Deng et al.

(10) Patent No.: US 11,491,233 B2
(45) Date of Patent: Nov. 8, 2022

(54) RESPONSIVE ELASTIC POLYMERS AND METHODS OF MAKING AND USING SAME

(71) Applicant: Purdue Research Foundation, West Lafayette, IN (US)

(72) Inventors: Meng Deng, West Lafayette, IN (US); Liangju Kuang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/309,141

(22) PCT Filed: Jun. 13, 2017

(86) PCT No.: PCT/US2017/037248
§ 371 (c)(1),
(2) Date: Dec. 12, 2018

(87) PCT Pub. No.: WO2017/218532
PCT Pub. Date: Dec. 21, 2017

(65) Prior Publication Data
US 2019/0184024 A1    Jun. 20, 2019

Related U.S. Application Data

(60) Provisional application No. 62/349,475, filed on Jun. 13, 2016, provisional application No. 62/366,160, filed on Jul. 25, 2016.

(51) Int. Cl.
| | |
|---|---|
| *A61K 47/61* | (2017.01) |
| *A61L 27/20* | (2006.01) |
| *A61L 27/18* | (2006.01) |
| *A61L 27/38* | (2006.01) |
| *A61L 27/54* | (2006.01) |
| *A61L 27/52* | (2006.01) |
| *A61L 27/26* | (2006.01) |
| *A61K 9/00* | (2006.01) |
| *A61K 9/06* | (2006.01) |
| *A61K 31/485* | (2006.01) |
| *A61K 47/36* | (2006.01) |
| *C08F 251/00* | (2006.01) |

(52) U.S. Cl.
CPC ............ *A61K 47/61* (2017.08); *A61K 9/0019* (2013.01); *A61K 9/06* (2013.01); *A61K 31/485* (2013.01); *A61K 47/36* (2013.01); *A61L 27/18* (2013.01); *A61L 27/20* (2013.01); *A61L 27/26* (2013.01); *A61L 27/3817* (2013.01); *A61L 27/3834* (2013.01); *A61L 27/52* (2013.01); *A61L 27/54* (2013.01); *C08F 251/00* (2013.01); *A61L 2300/414* (2013.01); *A61L 2300/64* (2013.01); *A61L 2430/02* (2013.01); *A61L 2430/06* (2013.01)

(58) Field of Classification Search
None
See application file for complete search history.

(56) References Cited

U.S. PATENT DOCUMENTS

| | | | |
|---|---|---|---|
| 6,630,457 B1 * | 10/2003 | Aeschlimann ....... | A61K 31/728 435/243 |
| 2005/0244363 A1 | 11/2005 | Hossainy et al. | |
| 2012/0183567 A1 | 7/2012 | Yasugi et al. | |

OTHER PUBLICATIONS

Tan et al (Biomaterials 30:6844-6853, 2009) (Year: 2009).*
Jin et al (Acta Biomaterialia 6:1968-1977, 2010) (Year: 2010).*
Kim et al (J Biomedical Materials Research Part A, 88A:967-975, 2009) (Year: 2009).*
Tan et al (Materials 3:1746-1767, 2010) (Year: 2010).*

* cited by examiner

*Primary Examiner* — Craig D Ricci
(74) *Attorney, Agent, or Firm* — Reichel Stohry Dean LLP; Natalie J. Dean; Mark C. Reichel

(57) ABSTRACT

Disclosed herein are functionalized hyaluronic acid (HA), a responsive elastic polymer system comprising functionalized HA, and methods of fabrication and utilization of the same. This polymer system may be used for controlled local or systemic drug delivery release of analgesics, anesthetics, antibiotics and other drugs as well as tissue engineering articles.

5 Claims, 27 Drawing Sheets

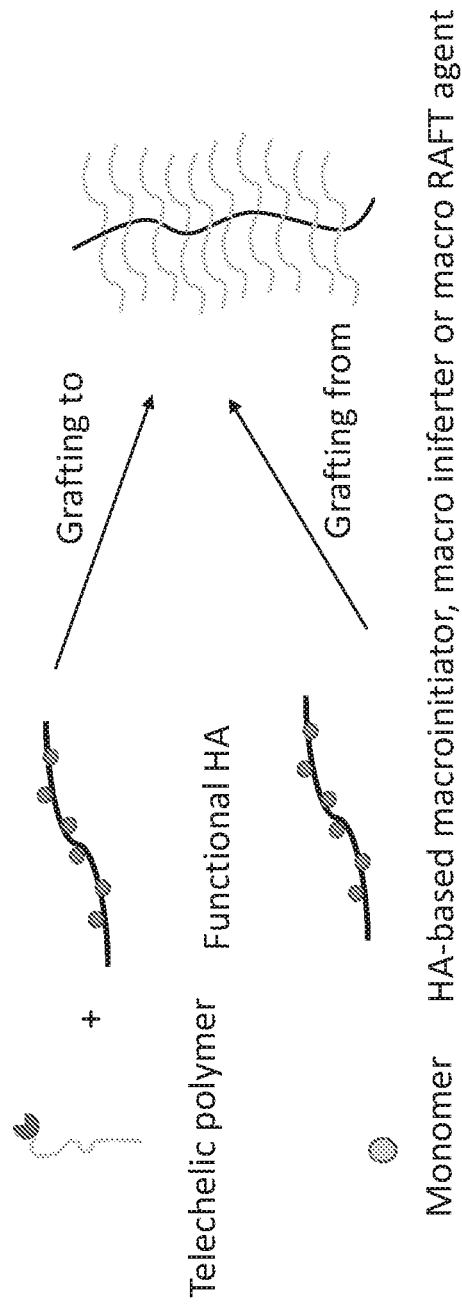
Figure 1. A schematic illustration depicting synthetic pathways of the hyaluronic acid based polymer matrix.

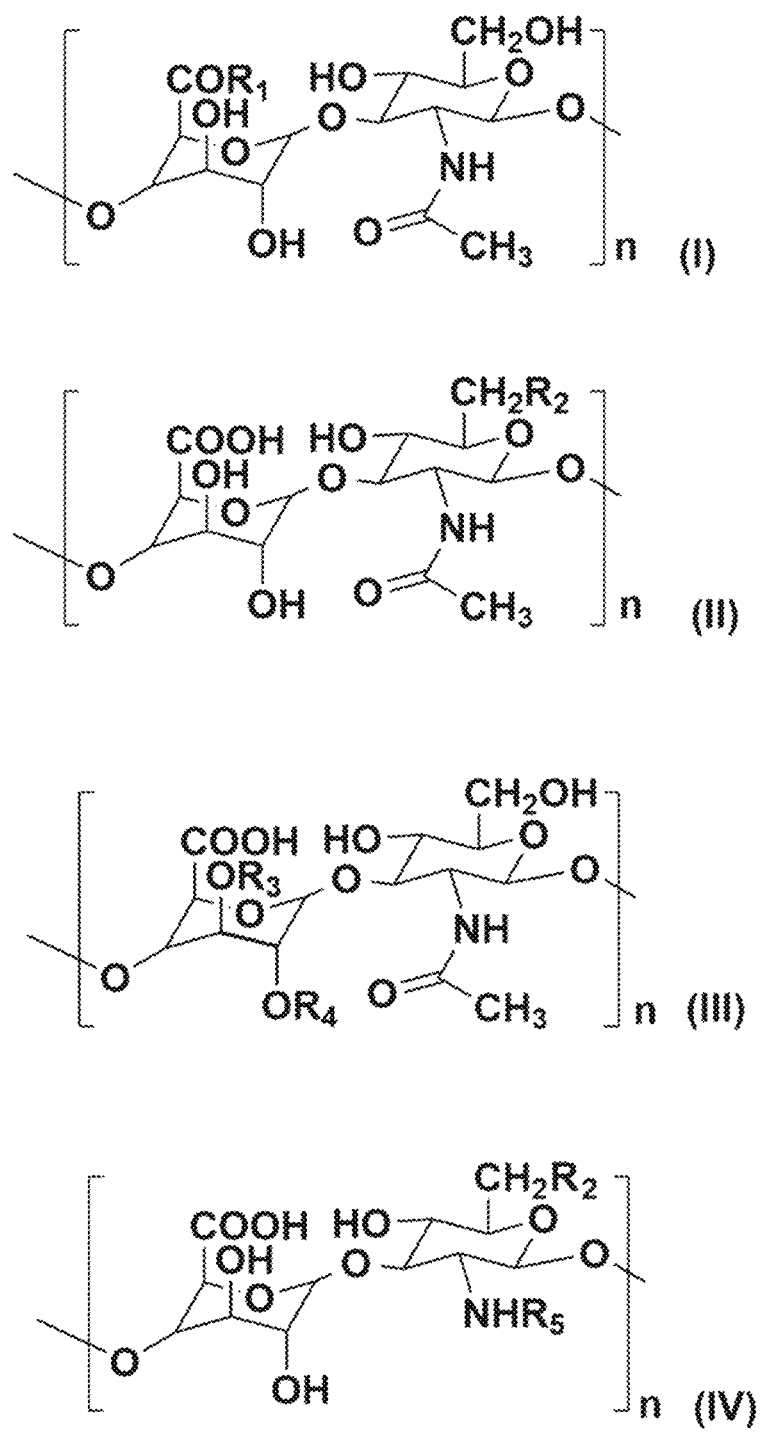
Figure 2. Functionalized monomeric hyaluronic acid represented by formula I, II, III, IV.

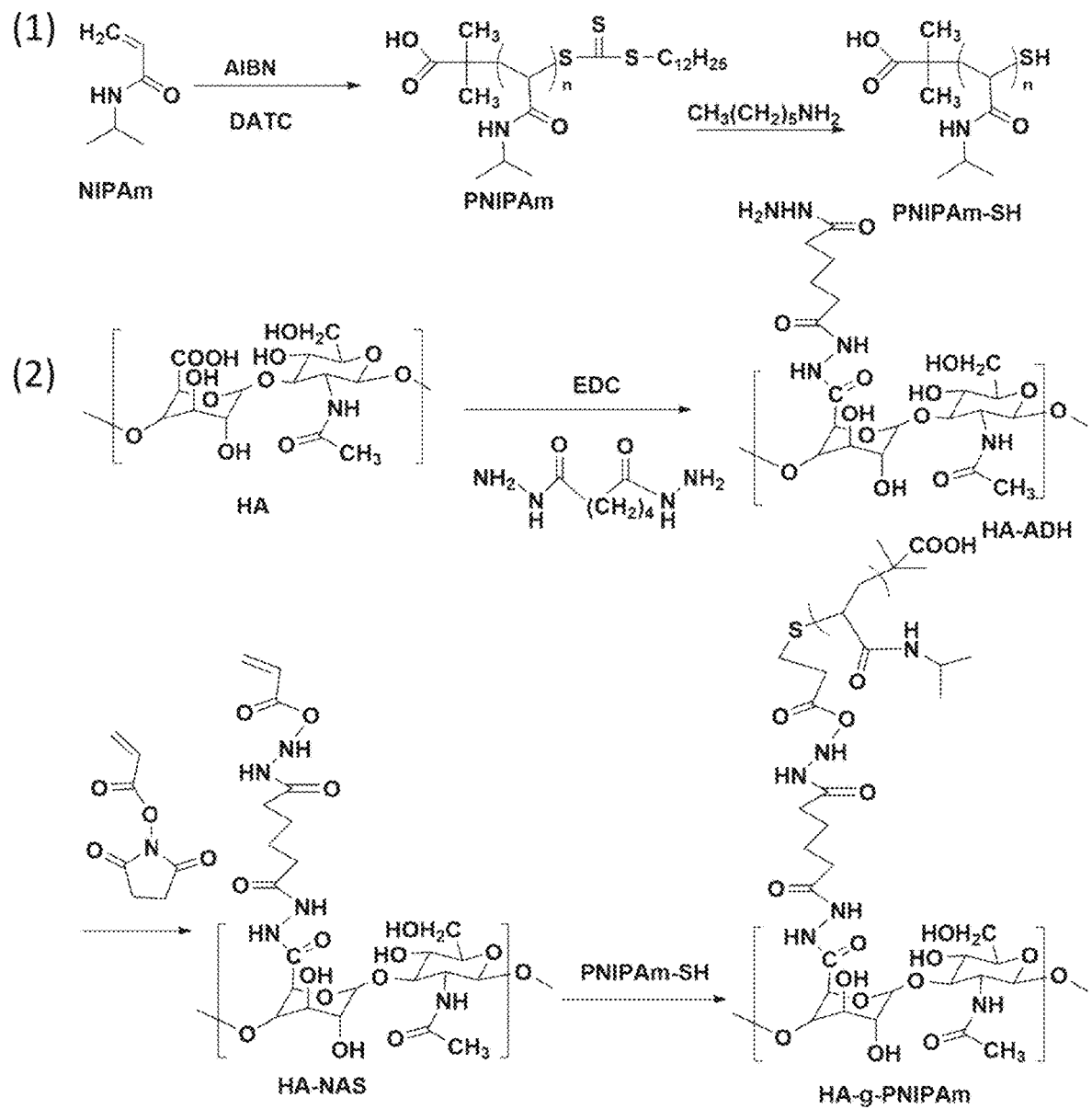
Figure 3. Synthesis of HA-g-PNIPAm via the combination of reversible addition-fragmentation chain transfer (RAFT) polymerization and thiol-ene click reaction Alternatively (2)

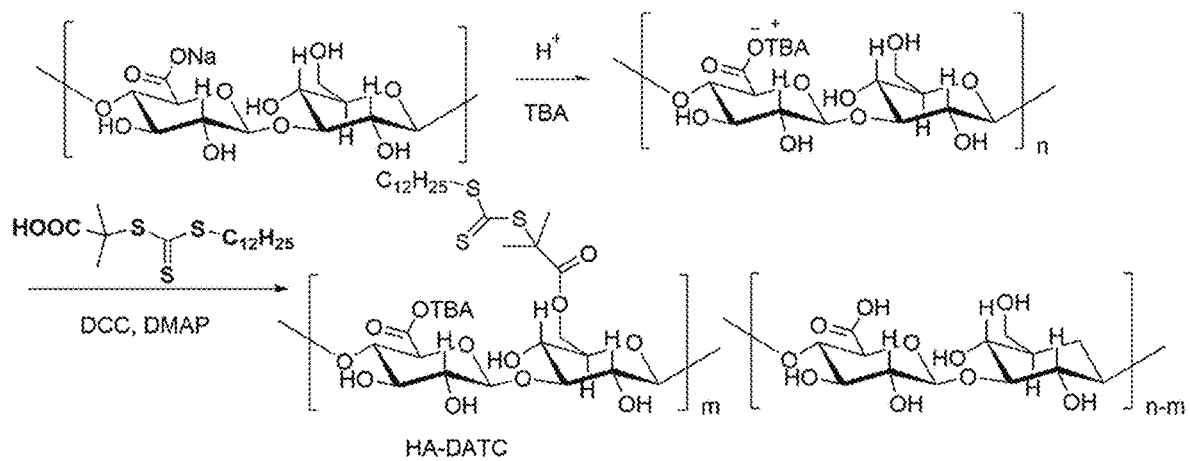
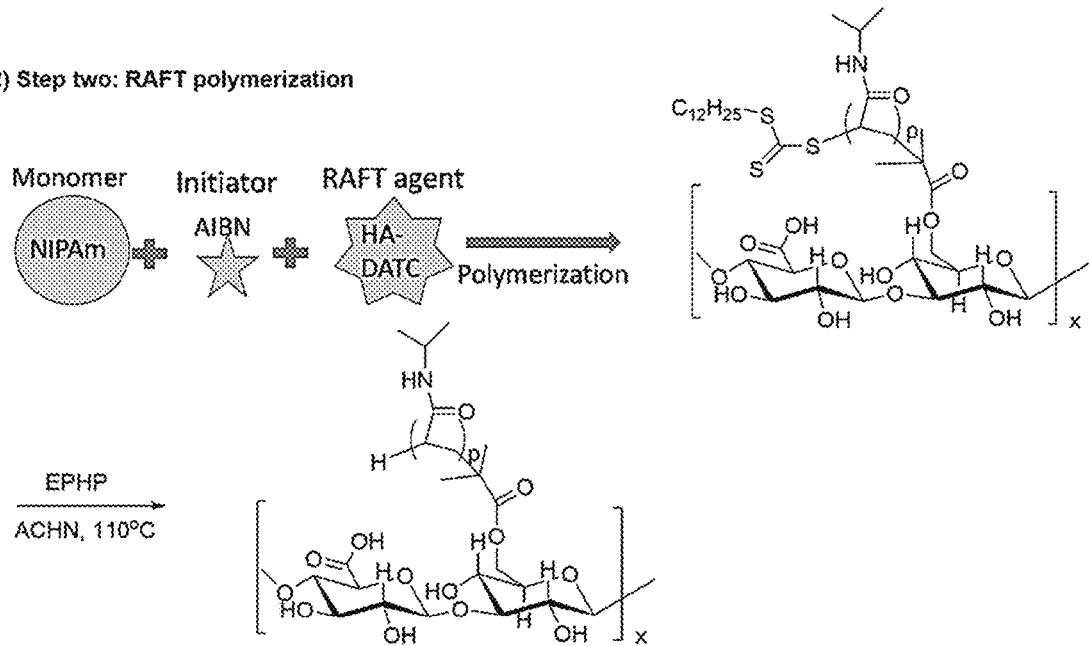
Figure 4. Synthesis of HA-g-PNIPAm via a 'grafting from' method using the reversible addition-fragmentation chain transfer (RAFT) polymerization

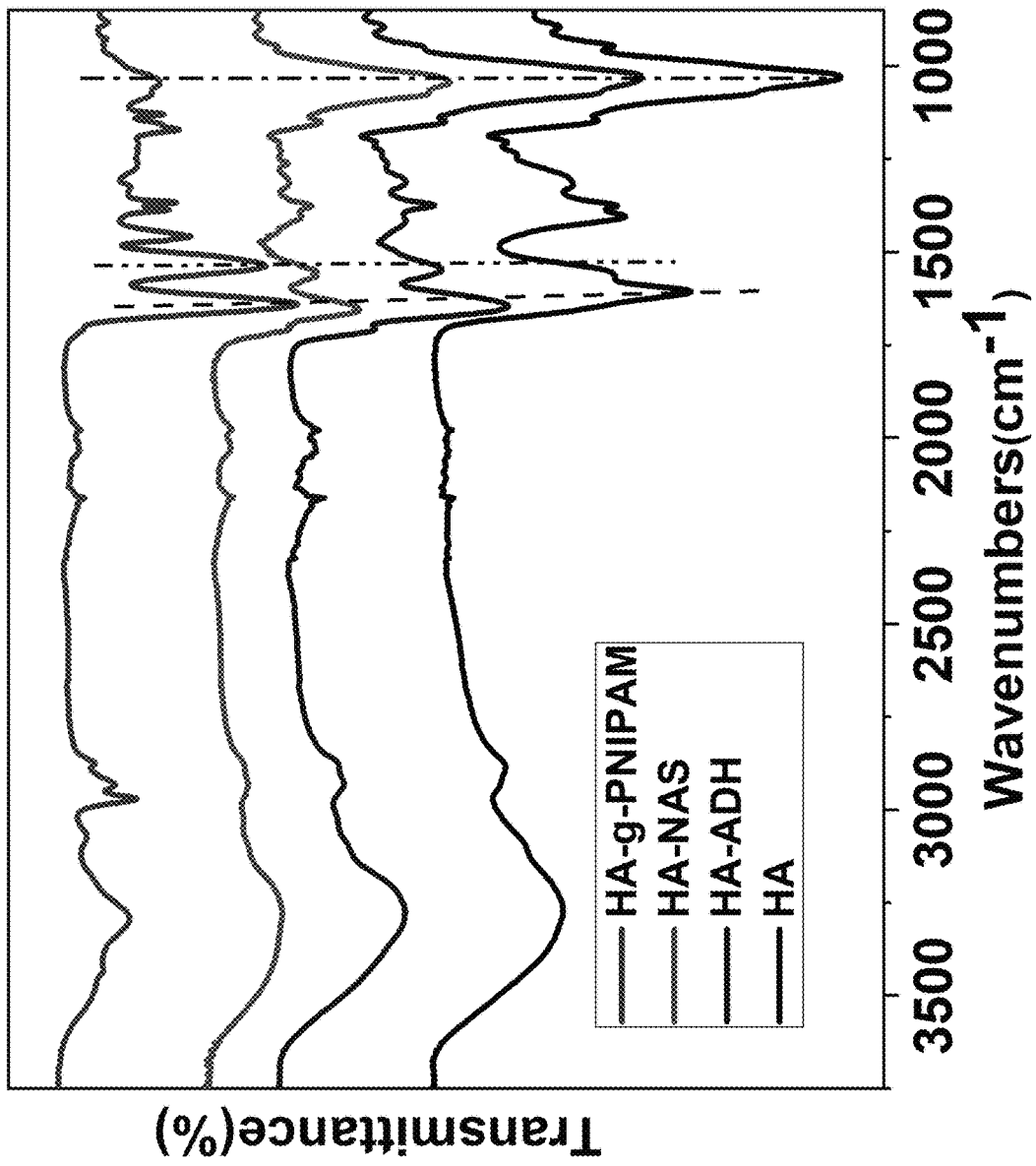
Figure 6. FTIR spectra of HA(black line), HA-ADH(blue line), HA-NAS(pink line) and HA-g-PNIPAm(red line), demonstrating successful synthesis of each step.

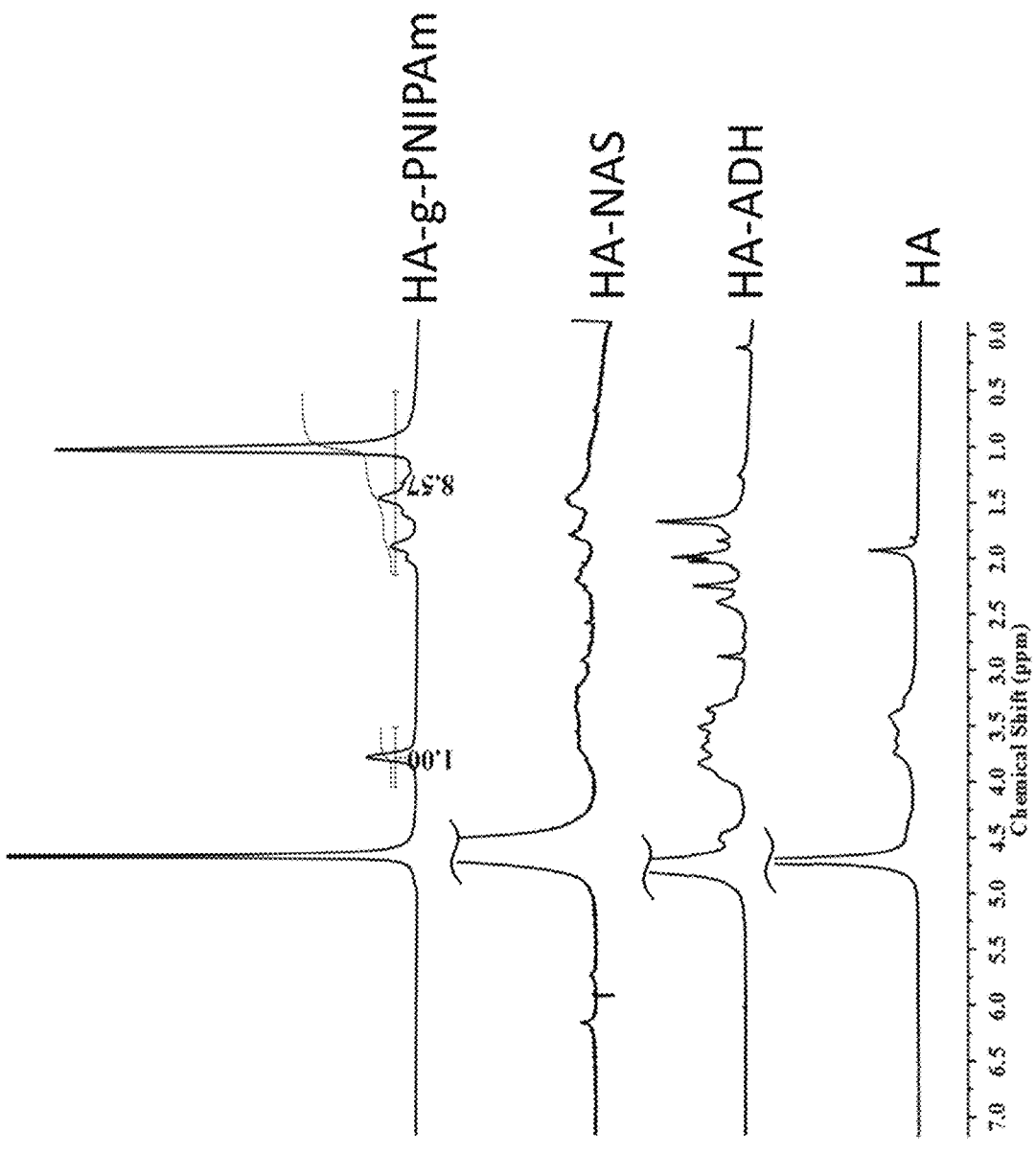
Figure 7. ¹H NMR spectra of HA, HA-ADH, HA-NAS and HA-g-PNIPAm, demonstrating successful synthesis of each step (∼ indicating truncated data).

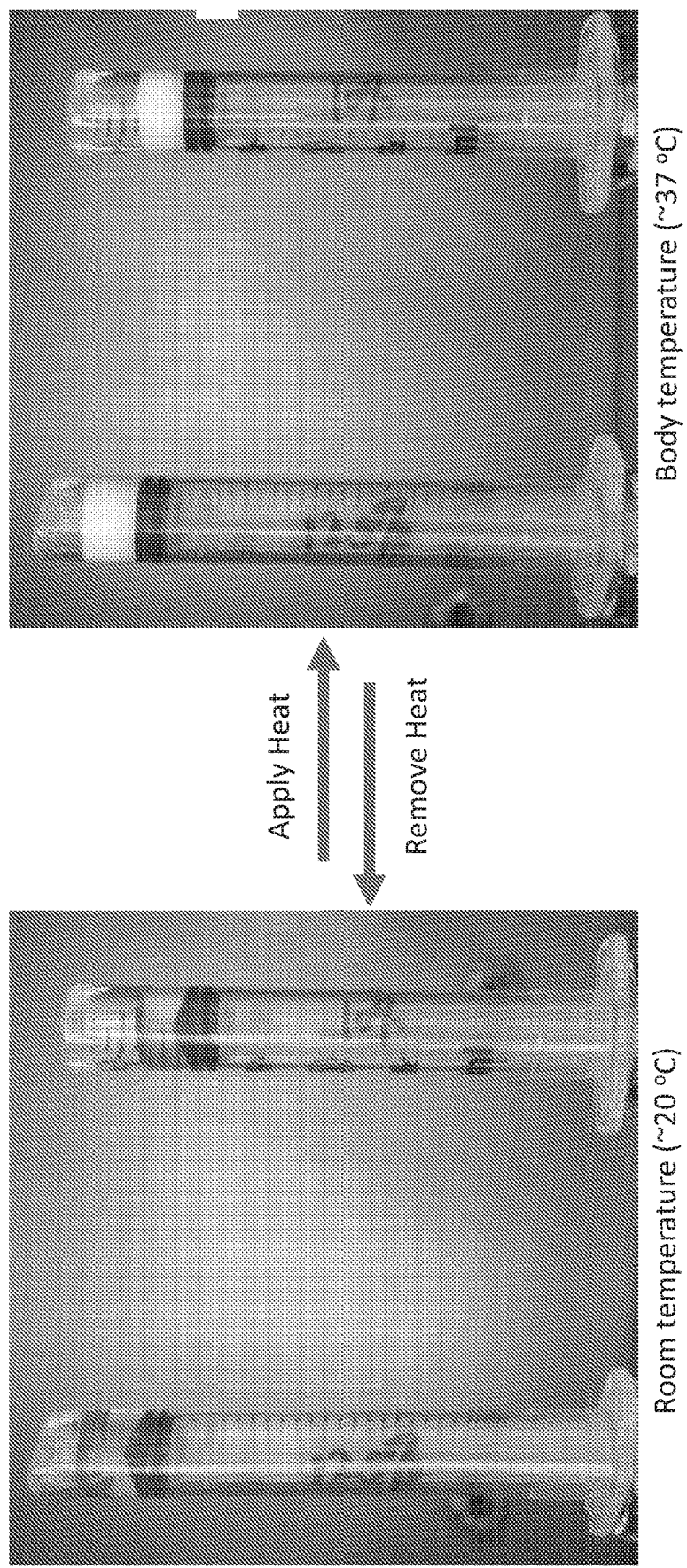
Figure 8. Reversibility of HA-g-PNIPAm hydrogels

Figure 9. HA-g-PNIPAm hydrogel formation confirmation

Figure 10. Characterization: Compressibility/Elasticity
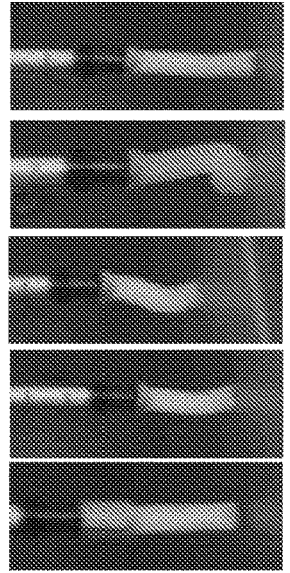
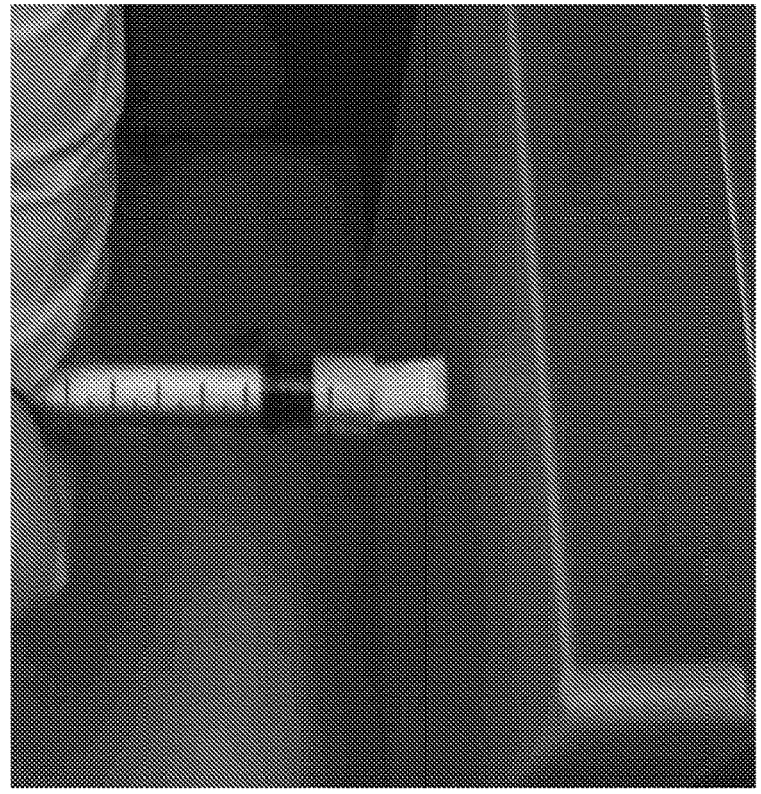
Time course pictures of HA-g-PNIPAm hydrogel with loading and unloading at 37°C, demonstrating the elastic nature of hydrogels.

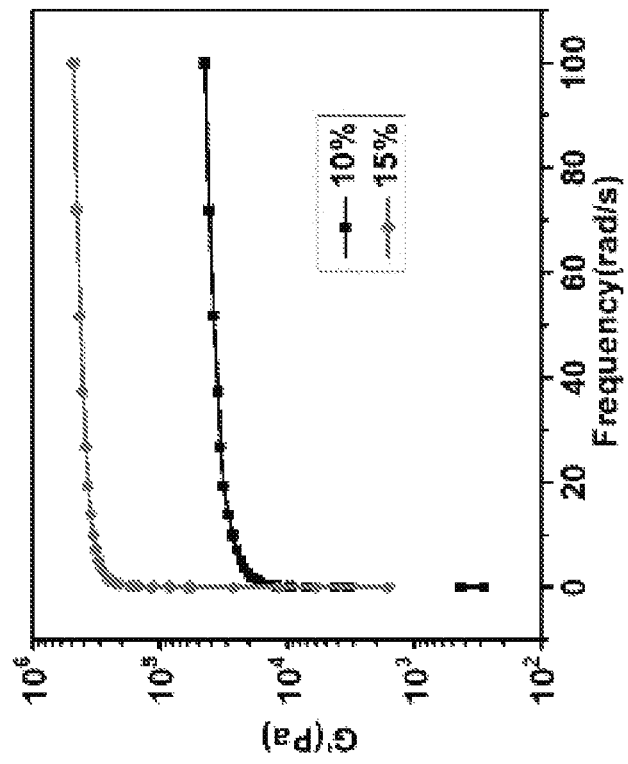
Figure 11. Frequency sweeps of HA-g-PNIPAm(13k) hydrogels. The linear modulus plateau with respect to frequency was determined. As the concentration of HA-g-PNIPAm increase, the gel stiffness increases.

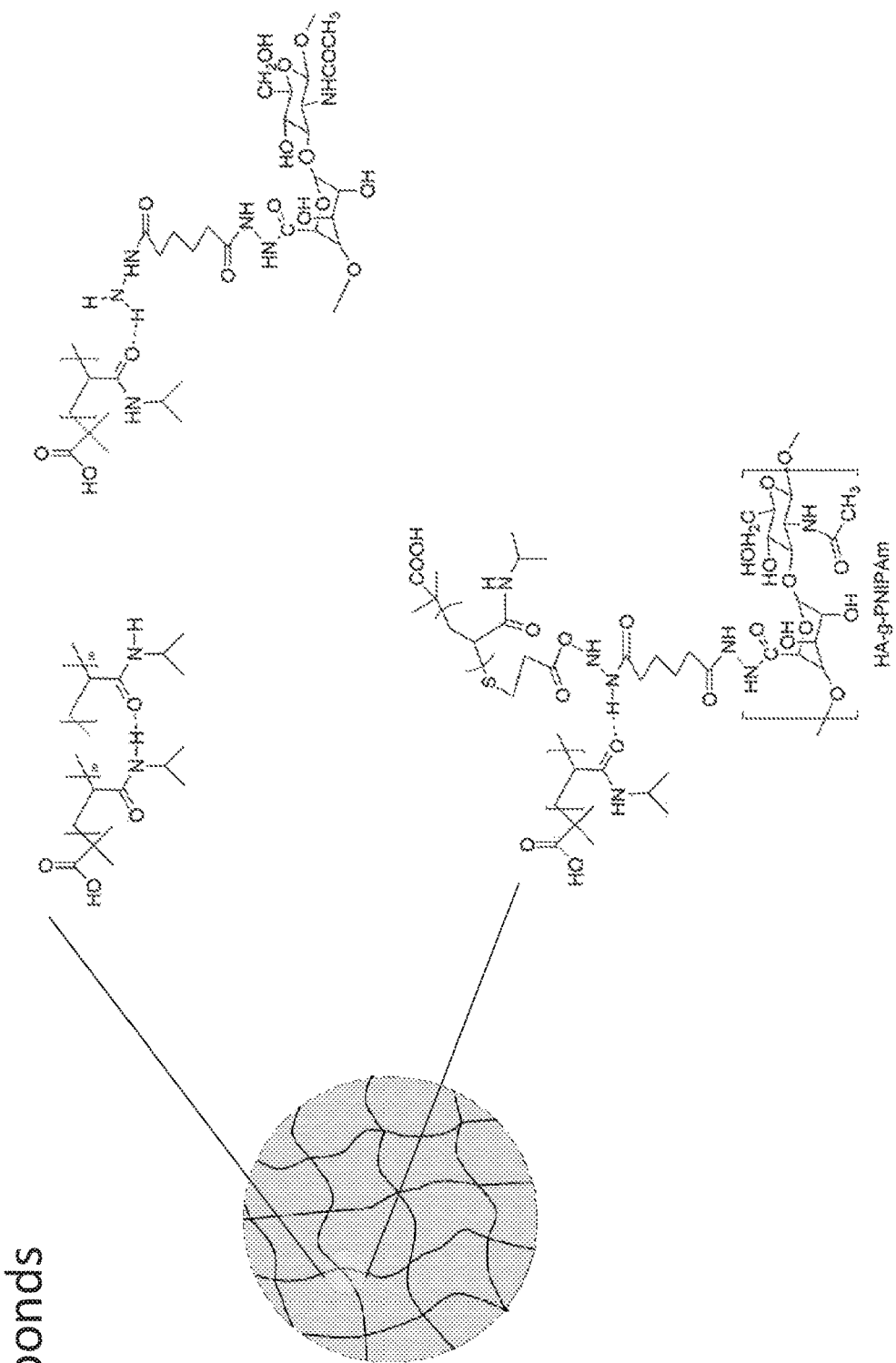
Figure 12. The proposed mechanism of HA-g-PNIPAm gels formation: the formation of intra- and intermolecular Hydrogen bonds

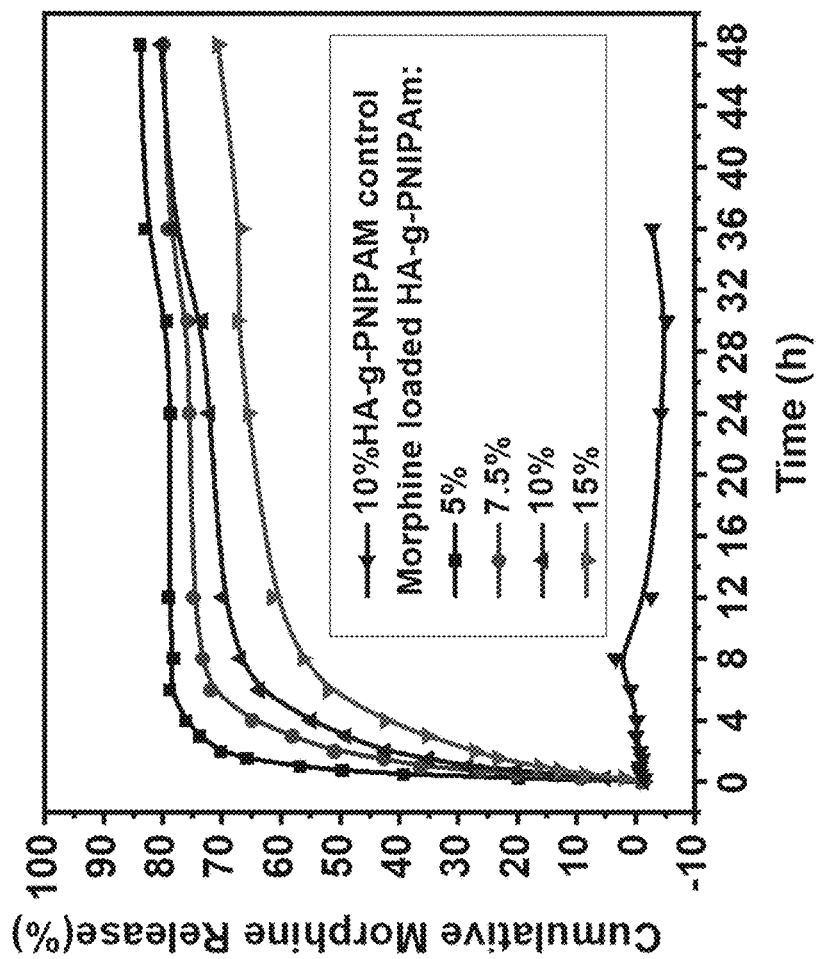
Figure 13. In vitro release profile of morphine from morphine loaded HA-g-PNIPAm (13k) with the concentration (w/v) 5%, 7.5%, 10% and 15% respectively, HA-g-PNIPAm (13k) hydrogels control, and morphine control. Morphine concentration is 0.468% (w/v). As the concentration of HA-g-PNIPAm increases, slower release of morphine.

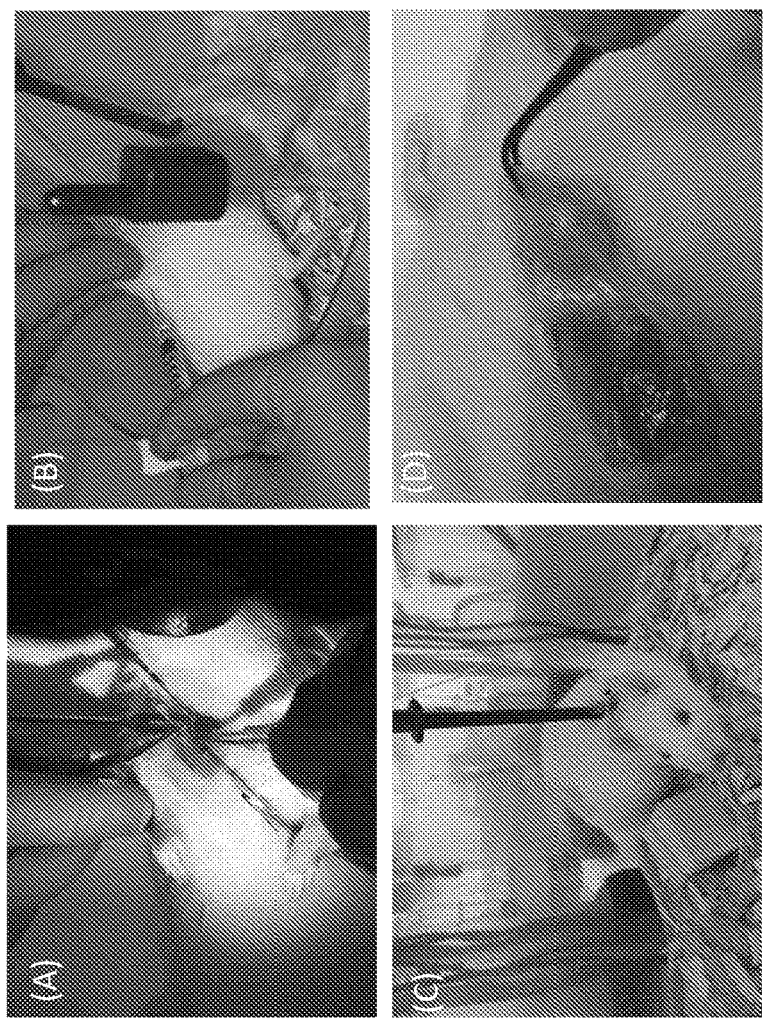

Figure 14. (A) Carotid artery catheterization surgery; (B) Subcutaneous injection of HA-g-PNIPAm and morphine solution into rats; (C) Blood samples were collected points using carotid artery placement method; and (D)Recovered tissues showing pockets of hydrogels were visible after 3 days of subcutaneous injections(0.25mL) confirming the hydrogel formation following subcutaneous injections.

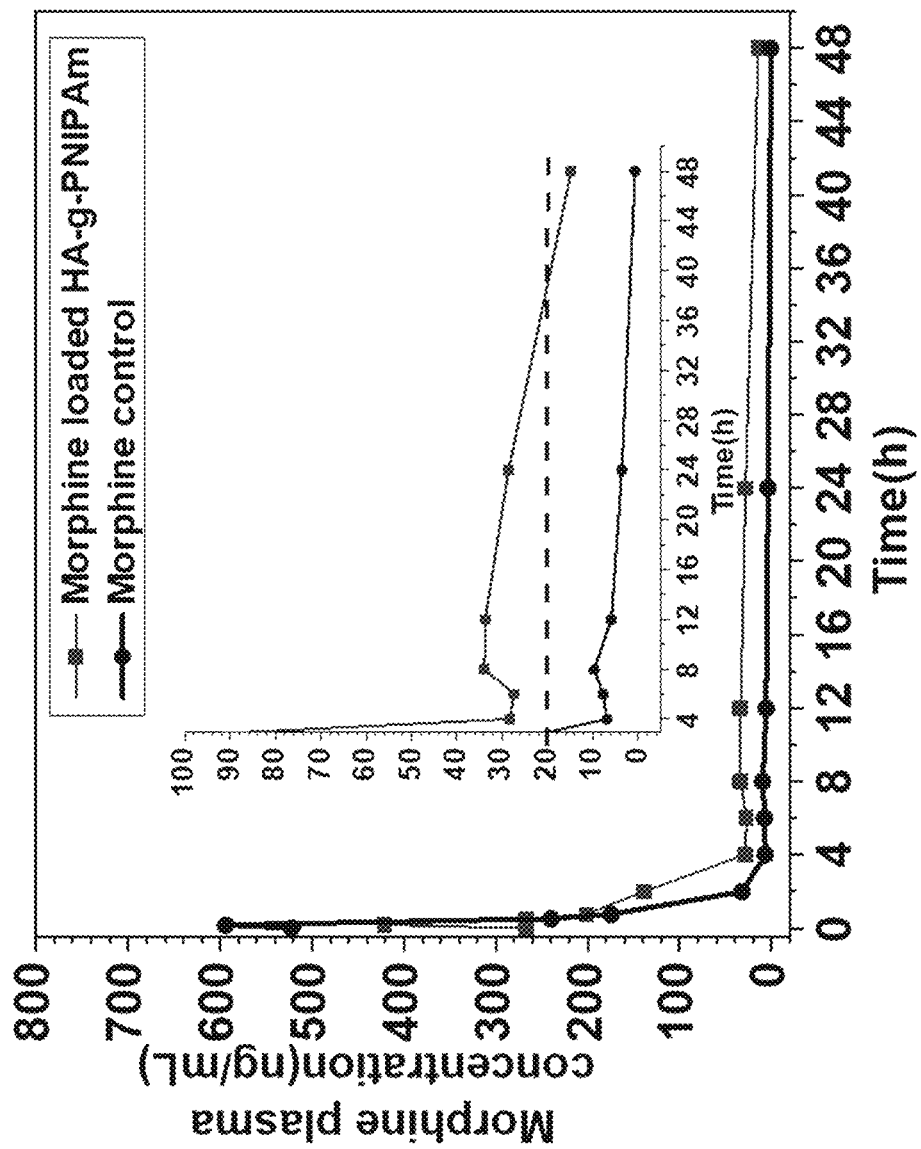
Figure 15. In vivo drug release profile following subcutaneous injections(0.25mL) in rats. The morphine plasma concentration(ng/ml) as a function of time. The blue line indicates the therapeutic plasma concentration (10ng/mL).

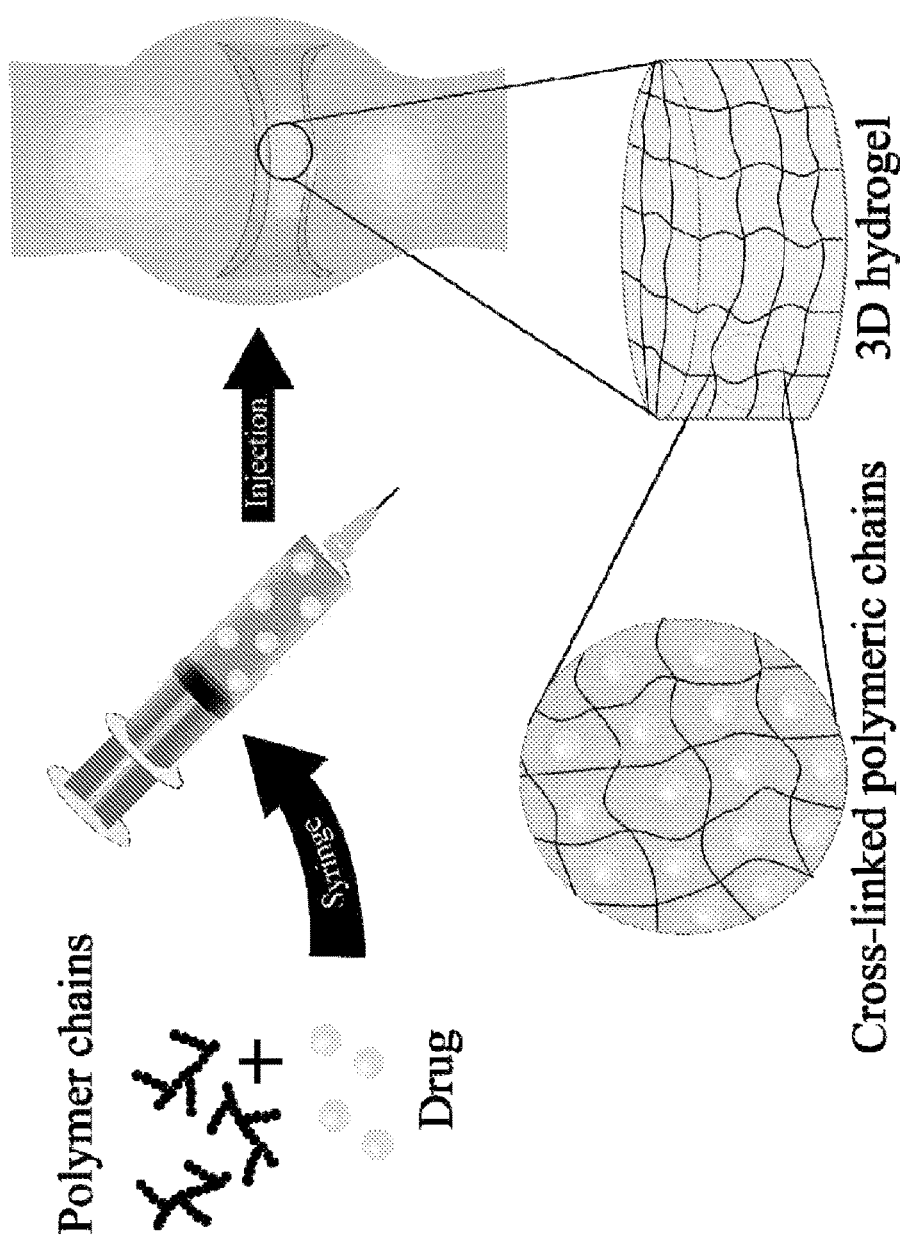
Figure 16. Schematics of injectable hydrogels for intraarticular delivery of an analgesic or anesthetic

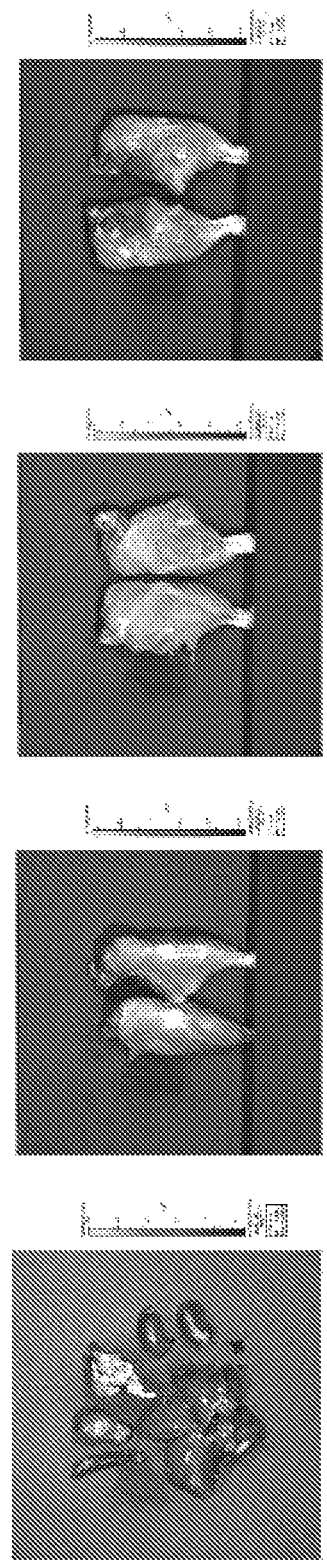

RESPONSIVE ELASTIC POLYMERS AND METHODS OF MAKING AND USING SAME

CROSS-REFERENCE TO RELATED APPLICATIONS

This application is a US National Phase filing of PCT/US2017/037248, filed on Jun. 13, 2017, which claims the benefits of U.S. provisional application 62/349,475, filed on Jun. 13, 2016 and U.S. provisional application 62/366,160, filed on Jul. 25, 2016. The contents of which are expressly incorporated herein entirely.

TECHNICAL FIELD

The present disclosure generally relates to polymer systems, and in particular to functionalized hyaluronic acid (HA), a responsive elastic polymer system which includes functionalized HA, and methods of its fabrication and utilization.

BACKGROUND

This section introduces aspects that may help facilitate a better understanding of the disclosure. Accordingly, these statements are to be read in this light and are not to be understood as admissions about what is or is not prior art.

Controlled drug delivery offers numerous advantages compared to conventional dosage forms including improved efficacy, reduced toxicity, reduced need for specialized drug administration (e.g. repeated injections), and improved patient compliance and convenience [1]. Several biomaterial-based controlled systems such as polymersomes, polymeric micelles, microspheres, nanospheres, nanoparticles, polymeric films, and silica nanoparticles are currently investigated to deliver drugs in a spatiotemporally controlled manner. Hydrogels composed of polymer networks swollen in water provide a promising delivery platform for controlled drug release applications because depot formulations can be created to allow drugs to slowly elute, maintaining a high local concentration of drug in the surrounding tissues over an extended period [2]. In addition, such hydrogels may also be used for controlled systemic drug release. Because responsive hydrogels that can respond simultaneously to triggers, such as pH, temperature, light, ions, and protein, they represent attractive candidate materials for development of drug delivery vehicles to achieve prolonged action [3].

However, the utility of conventional hydrogels for clinical applications is often hampered by their inferior mechanical performance. For instance, in general they are very weak and do not exhibit high stretch ability [4]. Consequently, it presents a grand challenge to use the conventional hydrogels in load-bearing anatomic sites like synovial joints. To function effectively in those settings, the hydrogel has to be stretchable and expandable under compression and tension without breaking. There is therefore an unmet need for the development of responsive, highly elastic injectable hydrogels.

SUMMARY

This disclosure provides a composition comprising a polymer matrix comprising functionalized hyaluronic acid (HA) of at least 100 monomeric units cross-linked to at least one unit of a telechelic polymer.

In some embodiment, the aforementioned functionalized hyaluronic acid is selected from the group consisting of the formula of I-IV:

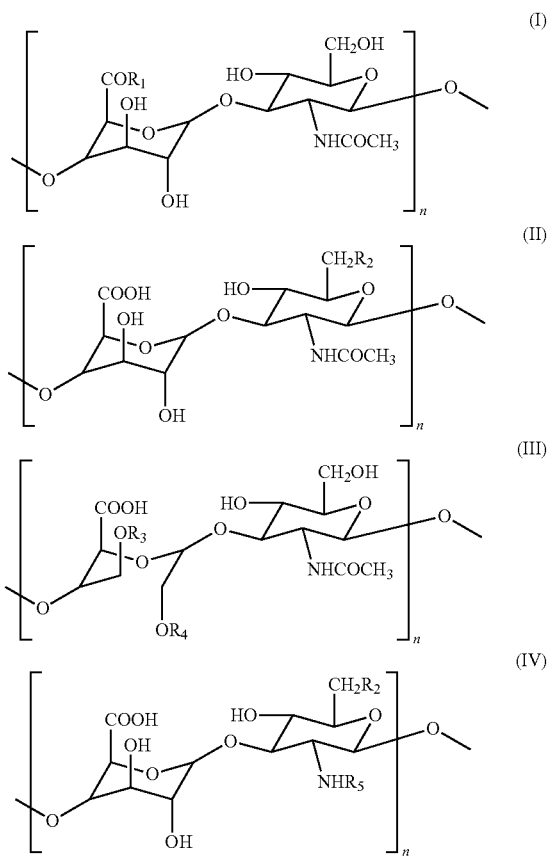

wherein $R_1$, $R_2$, $R_3$, $R_4$, and $R_5$ may include any one of or a combination of haloacetates, dihydrazides, amines, thiols, carboxylic acids, aldehydes, ketones, active hydrogen sites on aromatic ring, dienes, azide isothiocyanates, isocyanates, acyl azides, N-hydroxysuccinimide (NHS) esters, sulfo-NHS, sulfonyl chloride, epoxides, carbonates, aryl halides, imidoesters, carbodiimides (e.g. N, N'-dicyclohexylcarbodiimide (DCC) and 1-ethyl-3-(3-dimethylaminopropyl) carbodiimide (EDC)), alkylphosphate compounds, anhydrides, fluorophenyl esters, hydroxymethyl phosphines, guanidino groups, iodoacetyl derivatives, maleimides, aziridines, acryloyl derivatives, arylating agents, disulfide derivatives, vinylsulfone, phenylthioester, cisplatins, diazoacetates, carbonyl diimidazoles, oxiranes, N, N'-disuccinimidyl carbonates, N-hydroxylsuccinimidyl chloroformates, alkyl halogens, hydrazines, alkynes, and phosphorus-bound chlorine.

In some embodiment the aforementioned telechelic polymer is selected from the group consisting of any one of or a combination of poly (aliphatic ester) (e.g. poly(lactide) (PLA), poly(ε-caprolactone) (PCL), poly(glycolic acid) (PGA), poly(lactic-co-glycolic acid) (PLGA), poly(trimethylene carbonate) (PTMC), polydioxanone (PDS), poly(ortho ester), polyanhydrides, poly(anhydride-co-imide), poly(anhydride-esters), polyurethanes (e.g. degrapols), poly (amide), poly(esteramide), poly(orthoesters), poly(dioxanones), poly(acetals), poly(ketals), poly(carbonate), poly (orthocarbonates), poly(hydroxylbutyrates), poly(hydroxyl-valerats), poly(alkylene oxalates), poly(alkylene succunates), poly(malic acid), poly(amino acids), poly(vinylpyrrolidone), poly(hydroxycellulose), poly(glycerol sebacate), poly(ethylene imine), poly(acrylic acid)(PAA), poly(N,N'-diethylaminoethyl methacrylate, polyethylene glycol (PEG), poly(propylene oxide) (PPO), PEO-b-PPO block copolymers (e.g. pluronics (or poloxamers), and tetronic), poly(vinyl alcohol) (PVA), poly(N-isopropylacrylamide) (PNIPAm), Poly(N,N-diethylacrylamide) (PDEAAm), poly(oxazolines) (e.g. poly(2-methyloxazoline and poly(2-ethyl-2-oxazoline), oligo(ethylene glycol) fumarates (OPFs), poly(propylene fumarate), poly(alkyl cyanoacrylates), poly(acrylic amide), synthetic poly(amino acids) (e.g. poly(L-glutamic acid) (L-PGA) and poly (aspartic acid)), polyphosphazenes, and poly(phosphoesters).

In some embodiment the aforementioned telechelic polymer is selected from the group consisting of any one of or a combination of fibrin, collagen, matrigel, elastin, elastin-like peptides, albumin, natural poly (amino acids) (e.g. cyanophycin, poly (ε-1-lysine), poly (ɤ-glutamic acid)), polysaccharides (e.g. chitosan, dextran, chondroitin sulfate, agarose, alginate, methylcellulose, and heparin).

In some embodiment the aforementioned functionalized hyaluronic acid comprises at least one monomeric unit of hyaluronic acid functionalized with an amine moiety.

In some embodiment the aforementioned functionalized hyaluronic acid comprises at least one monomeric unit of hyaluronic acid functionalized with an acrylate moiety.

In some embodiment the aforementioned telechelic polymer is thiolated poly (N-isopropylacrylamide) PNIPAm.

This disclosure further provides a method of making a hyaluronic acid (HA) based polymer matrix comprising functionalized hyaluronic acid of at least 100 monomeric units cross-linked to at least one unit of a telechelic polymer. The method comprising the steps of:
preparing a functionalized hyaluronic acid of at least 100 monomeric units;
preparing a prefabricated functional telechelic polymer;
crosslinking the functionalized hyaluronic acid with the functional telechelic polymer by carbodiimide-mediated reactions, esterification, amidation, aldehyde and ketone reactions, active hydrogen reactions, photo-chemical reaction, azide-alkyne cycloaddition (e.g. copper-catalyzed azide-alkyne cycloaddition (CuAAC), copper-free azide-alkyne huisgen cycloaddition), thiol-click reaction, diels-alder reaction, nitrile oxide cycloaddition, and an enzymatic crosslinking strategy (e.g., horseradish peroxidase and hydrogen peroxide).

In some embodiment the aforementioned functional telechelic polymer is thiolated PNIPAm.

In some embodiment the aforementioned HA based polymer matrix further comprises at least one monomeric unit of a polymer which can be prepared by a polymerization reaction of i) the 'grafting to' and (ii) the 'grafting from' strategies.

In some embodiment the aforementioned crosslinking reaction between the functionalized hyaluronic acid and thiolated PNIPAm is a thiol-ene reaction.

In some embodiment the aforementioned 'grafting from' method involves the functionalized hyaluronic acid composing at least one of polymerizable moiety, an initiator, a RAFT agent and an infertier.

In some embodiment the aforementioned polymerizable moiety is an acrylate.

In some embodiment the aforementioned RAFT agent is S-1-dodecyl-S'-(α,α'-dimethyl-α''-acetic acid) trithiocarbonate (DATC).

In some embodiment the aforementioned polymerization reaction is a 'grafting from' method using surface initiated RAFT polymerization of PNIPAm.

This disclosure further provides a polymer-based drug delivery platform comprising aforementioned composition further encapsulating anesthetics, analgesics or antibiotic with the polymer matrix system through physical interactions or chemical interaction.

In some embodiment the aforementioned physical interactions comprise any one of or a combination of hydrophobic interaction, hydrophilic interaction, hydrogen bonding, and inter-molecular electrostatic interactions.

In some embodiment the aforementioned drug delivery platform comprises any one of opioids (e.g. morphine) or nonsteroidal anti-inflammatory drugs (NSAIDs) including chloroprocaine, bupivacaine, lidocaine, and procaine.

This disclosure further provides a method of controlled delivering a drug. The method comprising:
Preparing a polymer matrix comprising functionalized hyaluronic acid (HA) of at least 100 monomeric units cross-linked to a telechelic polymer with a theoretical substitution degree of a telechelic polymer ranging from 100% to 30%;
Preparing a polymer matrix comprising functionalized hyaluronic acid (HA) of at least 100 monomeric units cross-linked to a telechelic polymer with a theoretical substitution degree of amine group ranging from 20% to 80%;
Preparing the conjugation of the drug in the polymer matrix at a concentration ranging from 0-30% (w/v); and
Observing the drug release rate decreases with increasing molecular weight of the polymer matrix.

In some embodiment, the aforementioned drug delivery polymer matrix is HA-g-PNIPAm and the drug is morphine.

These and other features, aspects and advantages of the present invention will become better understood with reference to the following figures, associated descriptions and claims.

BRIEF DESCRIPTION OF THE FIGURES

FIG. 1 is a schematic illustration depicting synthetic pathways of hyaluronic acid based polymer matrix.

FIG. 2 shows a functionalized monomeric hyaluronic acid represented by formula I, II, III, IV.

FIG. 4 shows the synthesis of HA-g-PNIPAm via a 'grafting from' method using the reversible addition-fragmentation chain transfer (RAFT) polymerization.

FIG. 6 shows FTIR spectra of HA (black line), HA-ADH (blue line), HA-NAS (pink line) and HA-g-PNIPAm (red line), demonstrating successful synthesis of each step.

FIG. 7 shows $^1$H NMR spectra of HA, HA-ADH, HA-NAS and HA-g-PNIPAm, demonstrating successful synthesis of each step.

FIG. 8 shows reversibility of HA-g-PNIPAm hydrogels.

FIG. 9 shows HA-g-PNIPAm hydrogel forming confirmation.

FIG. 10 shows time course pictures of HA-g-PNIPAm hydrogel with loading and unloading at 37° C., demonstrating the elastic nature of hydrogels.

FIG. 11 shows frequency sweeps of HA-g-PNIPAm hydrogels. The linear modulus plateau with respect to frequency was determined. As the concentration of HA-g-PNIPAm increase, the gel stiffness increases.

FIG. 12 shows a proposed mechanism of HA-g-PNIPAm gels formation: the formation of intra- and intermolecular hydrogen bonds.

FIG. 13 shows an in vitro release profile of morphine from morphine loaded HA-g-PNIPAm (13 k) with the concentration (w/v) 5%, 7.5%, 10% and 15% respectively, and HA-g-PNIPAm (13 k) hydrogels control. Morphine concentration is 0.468% (w/v). As the concentration of HA-g-PNIPAm increases, slower release of morphine.

FIG. 14 shows Pharmacokinetics study of morphine in rats. (A) A carotid artery catheterization surgery; (B) Subcutaneous (s.c.) injection (0.25 mL) of morphine-loaded 10% HA-g-PNIPAm hydrogels; (C) Blood samples were collected points using an automated system (Culex) through preplaced carotid catheter; and (D) Recovered tissues showing pockets of hydrogels were visible after 3 days of subcutaneous injections (0.25 mL) confirming the hydrogel formation following subcutaneous injections.

FIG. 15 shows in vivo drug release profile following subcutaneous injections (0.25 mL) in rats. The morphine plasma concentration (ng/mL) as a function of time. The blue line indicates the therapeutic plasma concentration (10 ng/mL).

FIG. 16 shows schematics of injectable hydrogels for intraarticular delivery of an analgesic or anesthetic.

FIG. 26. Ex vivo fluorescence imaging of different tissues at 72 h post injection.

DESCRIPTION

Figure 3:
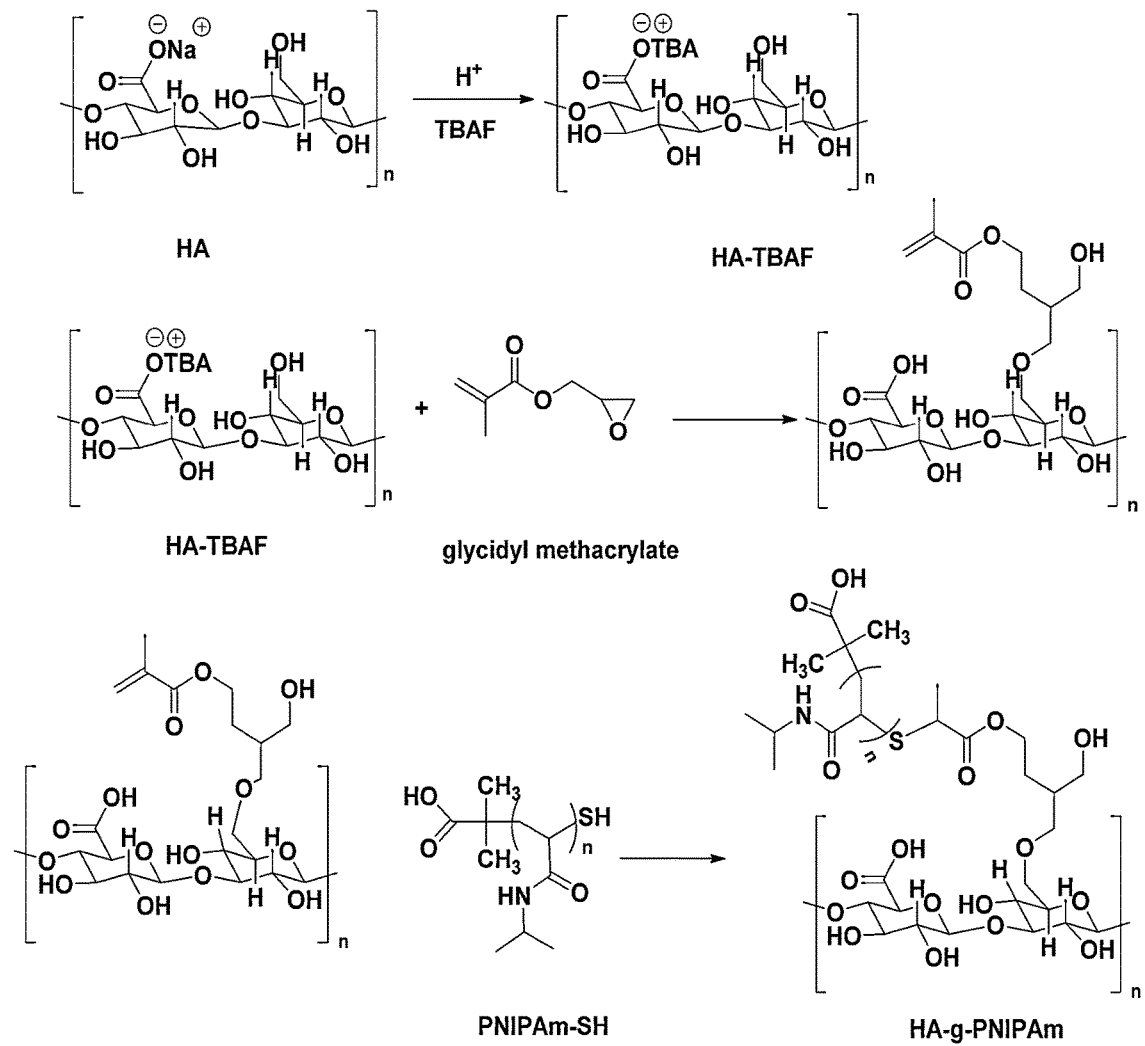
FIG. 3 shows the synthesis of HA-g-PNIPAm method via the combination of reversible addition-fragmentation chain transfer (RAFT) polymerization and thiol-ene click reaction.
Figure 5:
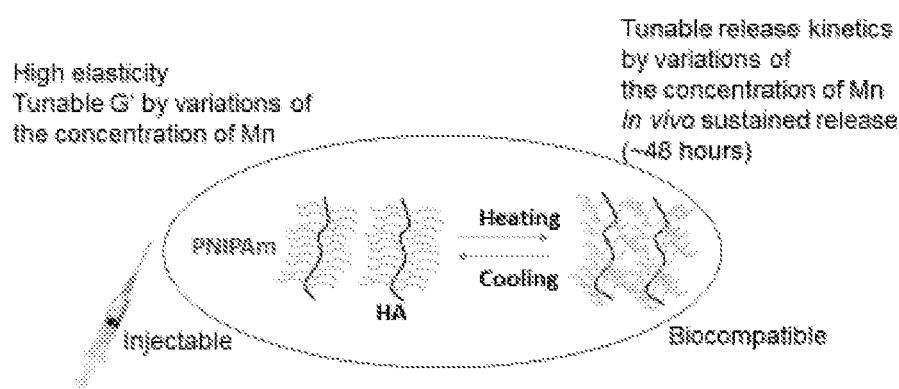
FIG. 5 shows a schematic illustration of the advantages of HA-g-PNIPAm hydrogels.
Figure 17:
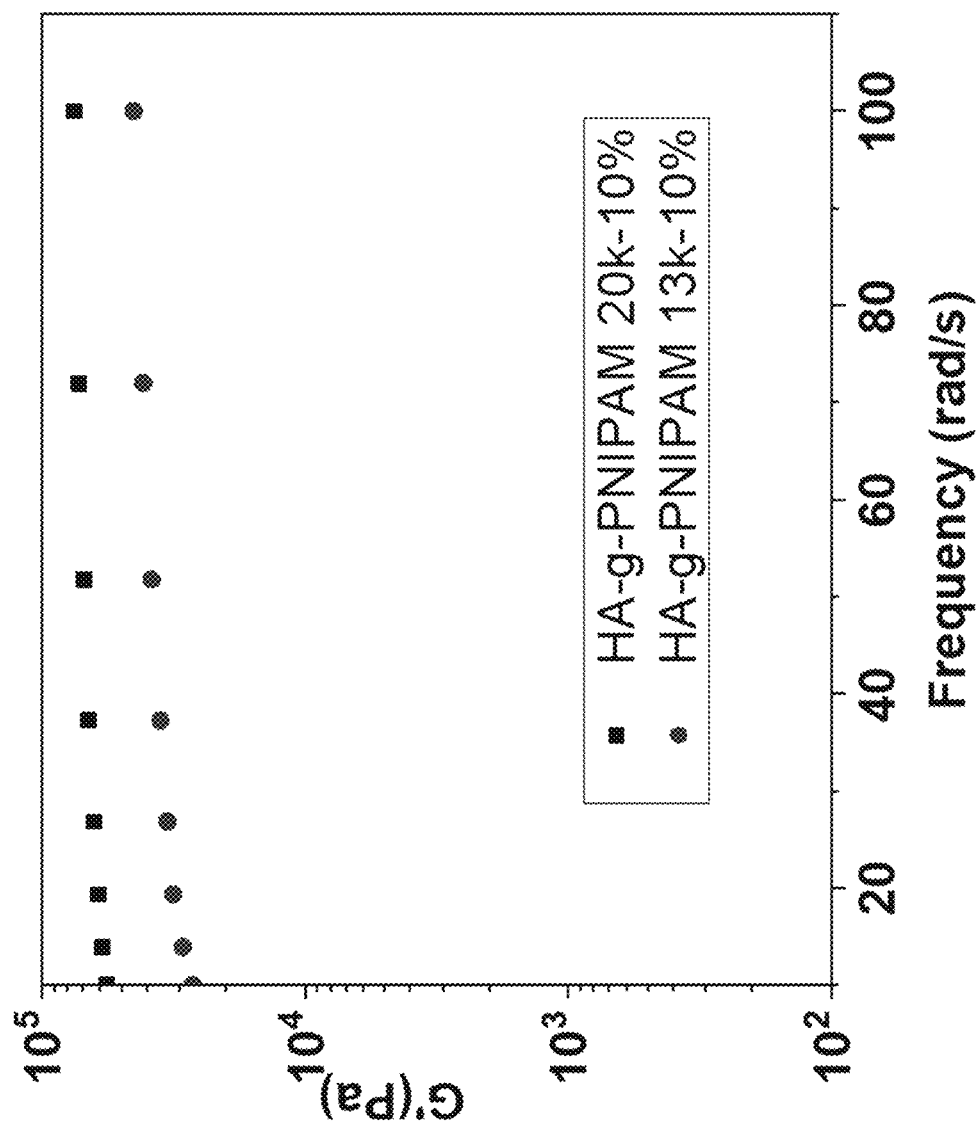
FIG. 17 Frequency sweeps of HA-g-PNIPAm hydrogels at the concentrations of 10% (w/v). The linear modulus plateau with respect to frequency was determined. As the molecular weight of HA-g-PNIPAm increase, the gel stiffness increases.
Figure 18:
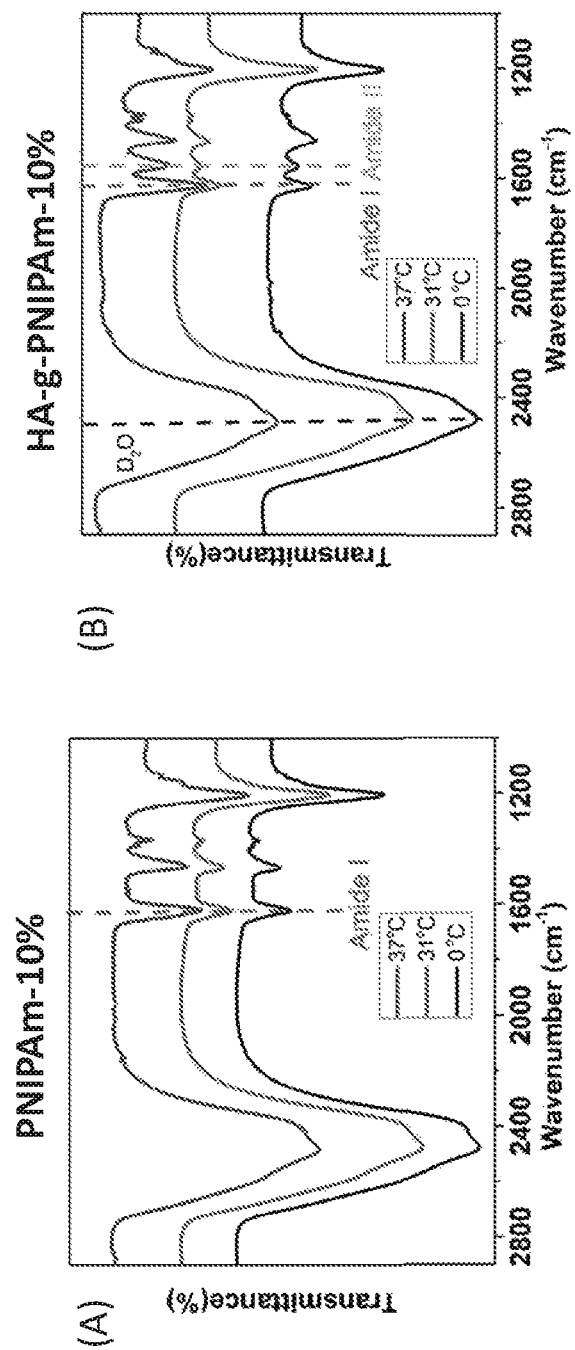
FIG. 18. (A) FTIR spectra of 10% PNIPAm (w/v) at temperature of 0° C., 31° C., and 37° C., respectively. (B) FTIR spectra of 10% HA-g-PNIPAm13 k (w/v) at temperature of 0° C., 31° C., and 37° C., respectively. The results indicates hydrogen bonding plays an important role in HA-g-PNIPAM hydrogel formation.
Figure 19:
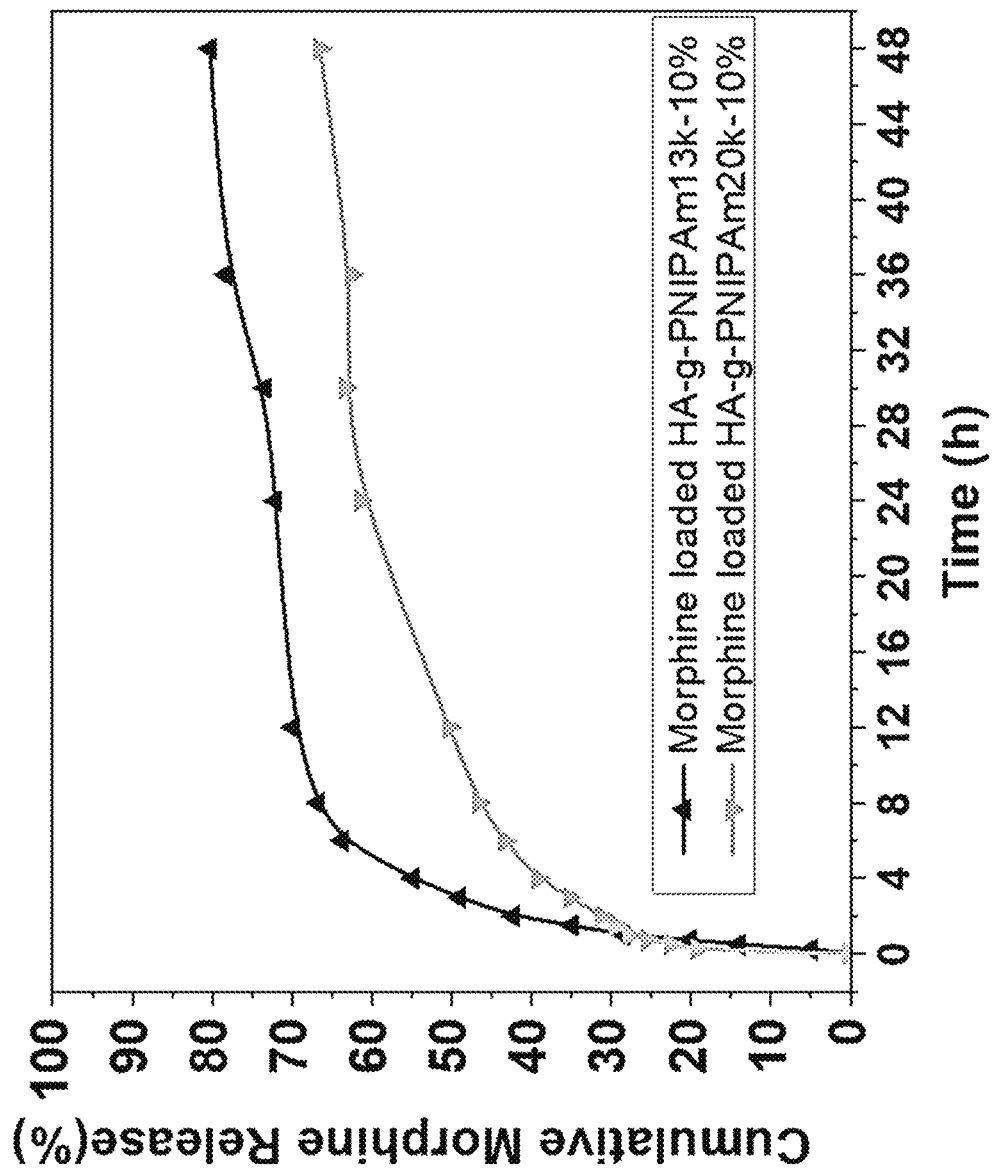
FIG. 19. In vitro release profile of morphine from morphine loaded HA-g-PNIPAm 13 k and 20 k, respectively. Morphine concentration is 0.468% (w/v). As the molecular weight of HA-g-PNIPAm increased, the release of morphine decrease.
Figure 20:
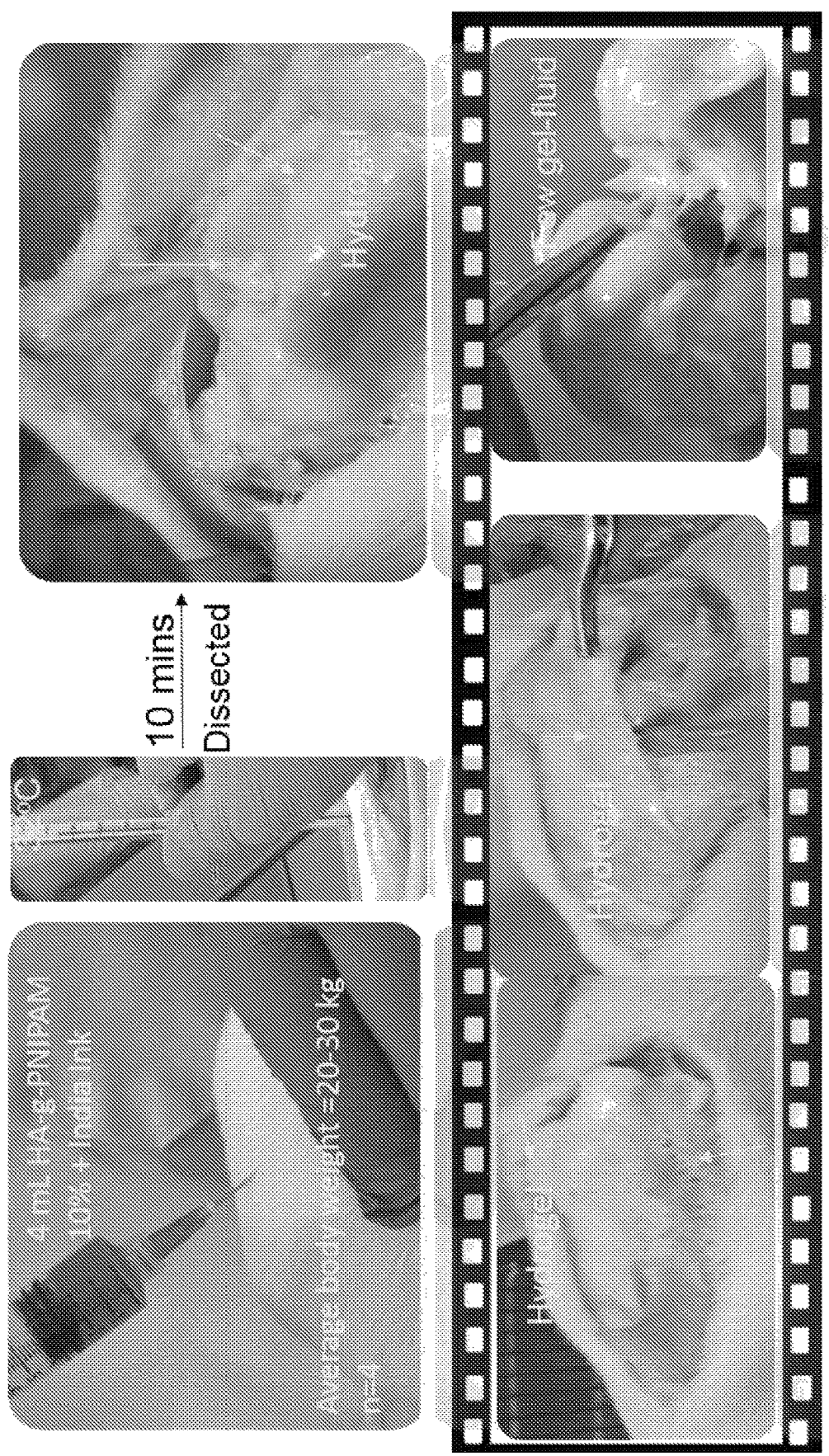
FIG. 20. Intra-articular injections into cadaver dogs. The hydrogels distributed well through the cranial compartment of the joint. The gel most likely will form thin sheets in the trochlear groove and on the lateral and medial side of the condyles.
Figure 21:
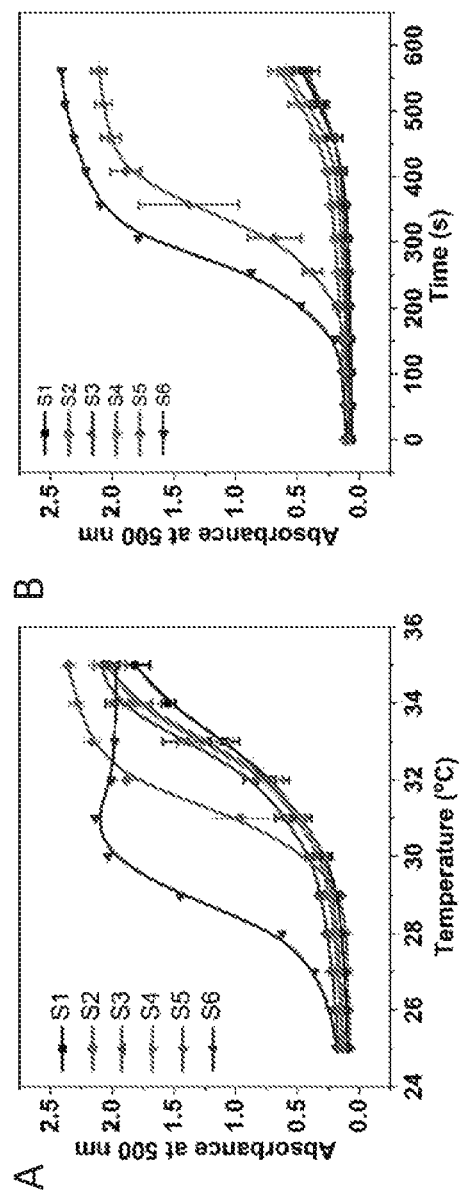
FIG. 21. Influence of the grafting density and concentrations of HA-g-PNIPAm on (A) gelation temperature and (B) gelation time. Theoretical substitution degrees (DS) of: S5 of 100%, S4 of 80%, S3 of 64%, S2 of 40%, and S1 of 30% at the concentrations of 10% (w/v). S6: at DS of 100% and at the concentrations of 15%.
Figure 22:
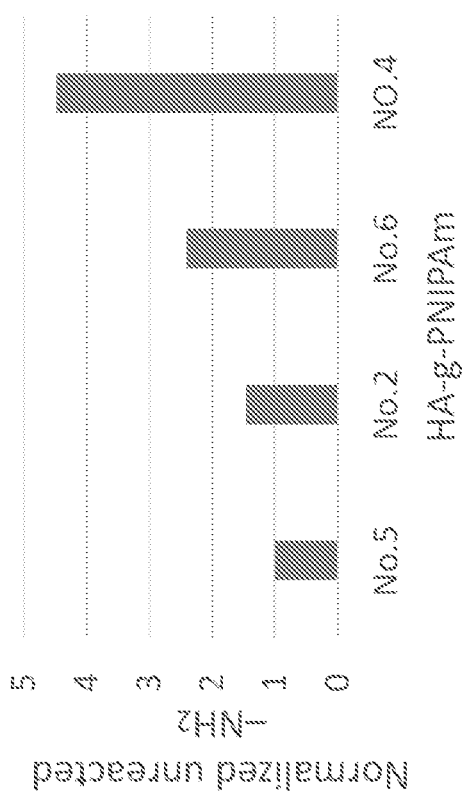
FIG. 22. Tunable amine groups in HA-g-PNIPAm17k (Structure No. 5, No. 2, No. 6 and No. 4 with PNIPAm DS of 100%, 40%, 50%, and 80% respectively.
Figure 23:
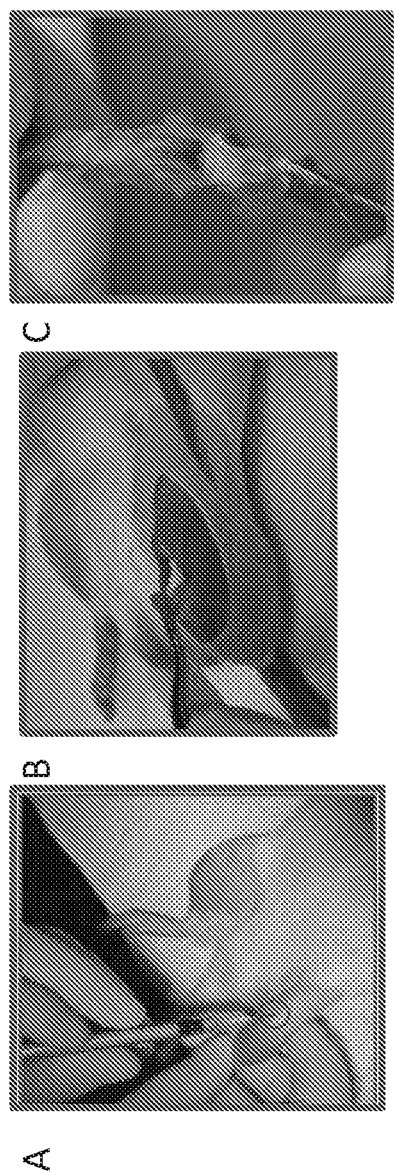
FIG. 23. Injectability and degradation of HA-g-PNIPAm hydrogels (at the concentration of 15% (w/v)) using a rat model. Photograph images show (A) Intra-articular injections into a rat. (B) Hydrogel formed right after injections. (C) Hydrogel degraded 21 day post injection.
Figure 24:
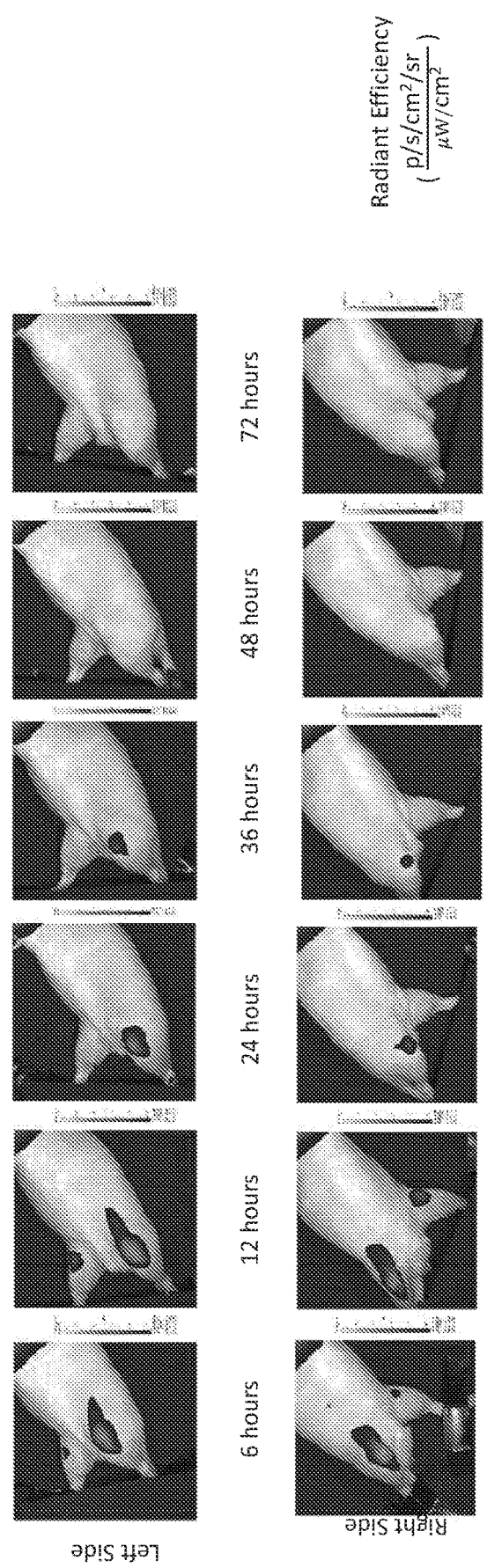
FIG. 24. Intravital fluorescence imaging of the release of Alexa Fluor 680 conjugated BSA from HA-g-PNIPAm hydrogels. (n=4)
Figure 25:
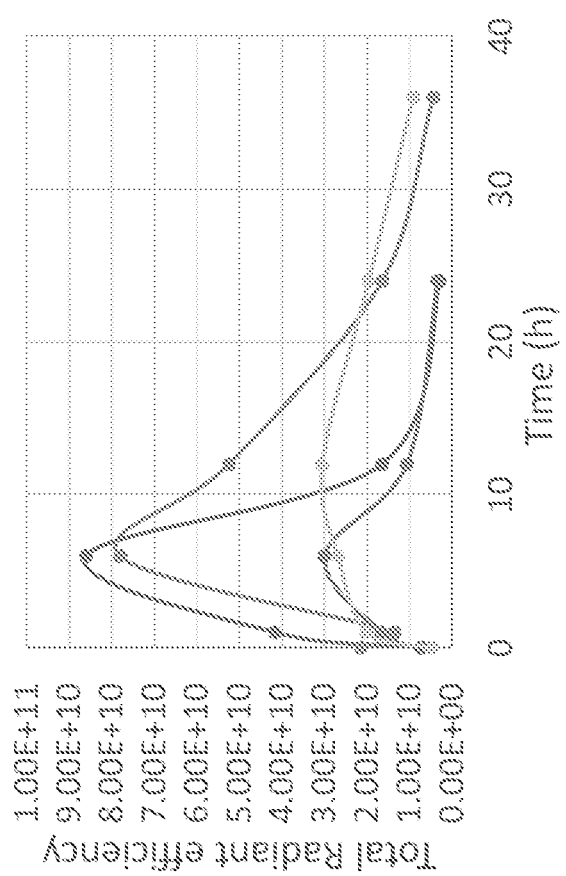
FIG. 25. Total radiant efficiency emanating from the knee joint as a function of time. Alexa Fluor 680 conjugated BSA (BSA-AF) released from the HA-g-PNIPAm hydrogels showed a maximum concentration post 6-12 hours intra-articular injections and sustained release profile, and the BSA-AF was detected in the knee joints for more than 24 hours.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

As used herein, "the degree of substitution" (DS) of substituent groups, (e.g., PNIPAm or amine groups) is the (average) number of substituent groups ((e.g., PNIPAm or a amine group) attached to total monomeric unit of polymers HA. for example, a theoretical DS of HA equals (number of substituent groups)/(number of monomeric unit of polymers HA). Since per monomeric unit of polymers HA contains one —COOH, the DS=(number of substituent groups)/(number of —COOH).

In response to the unmet need, the development of responsive, highly elastic injectable hydrogels that include functionalized hyaluronic acid (HA) is disclosed herein.

HA is an immunoneutral polysaccharide consisting of alternating disaccharide units of [$\beta$(1,4)-D-glucuronic acid-$\beta$(1,3)-N-acetyl-D-glucosamine) linkages [5]. HA is the only non-sulfated glycosaminoglycan that is widely distributed throughout the body, especially in the synovia of joints, the corpus vitreum of the eyes, and the dermis of the skin. HA is predominantly localized to the extracellular and pericellular matrix. Functionally, HA contributes to the elastoviscosity of fluid connective tissues including synovial fluid and vitreous humor, and modulates hydration and transport of water through tissues [6]. The enzymatic degradation of HA results from the action of three types of enzymes: hyaluronidase, $\beta$-glucuronidase, and $\beta$-nacetyl-hexosaminidase, which mainly accounts for HA derived hydrogel's biodegradable properties [7]. Additionally, HA has been used clinically for more than thirty years [8, 9]. For example, it has been approved by the US Food and Drug Administration for the treatment of osteoarthritis in humans since 1997[10].

Cross-linked HA-based polymeric biomaterials are widely used for drug delivery vehicles owing to the major advantages of HA including: (i) biodegradability and biocompatibility; (ii) ease of chemical modification due to an abundance of carboxylic acid and hydroxyl groups; (iii) high potential drug loading; (iv) its intrinsic targeting properties, due to the selective interactions with receptors, such as CD44, Toll2, Toll4, RAAMM receptor or hyaluronan receptors for endocytosis. (vi) HA degraded from HA-based polymeric biomaterials may serve as a lubricant and shock absorber in the joints. HA could stabilize the joint function due to its lubrication properties at low shear and increased friction at high shear. A thin layer of HA acts a shock absorber between cartilage and cartilage/meniscal surface. And (vii) HA coats pain receptors to prevent binding to peptide agonists [11, 12].

Cross-linked HA-based polymeric biomaterials may be used for tissue engineering due in part to their ability to efficiently encapsulate cells. Mechanical and structural properties may be manipulated by modification of the crosslinking density which controls network pore size, water content, mechanical properties, and cell-material interactions. In some cases, cross-linked polymers or gels may have a high, tissue-like water content which may allow nutrient and waste transport. HA has numerous useful biological properties within tissue integration including wound healing [13], cell adhesion and proliferation [14], cell motility, angiogenesis, cellular signaling, and matrix organization [9].

According to at least one embodiment, an HA-based polymer matrix can be prepared following two main strategies: (i) the 'grafting to' and (ii) the 'grafting from' strategies as shown in FIG. 1.

The 'grafting to' strategy involves the attachment of prefabricated polymers via either physiorption or covalent bond formation (chemisorption) [15]. HA can be modified in many ways to alter the properties of the resulting materials, including modifications leading to hydrophobicity and biological activities [10]. In part, the present disclosure provides for a composition comprising at least one monomeric unit of HA functionalized by at least one functional group moiety. Chemical modifications of HA can be targeted to three functional groups: the glucuronic acid carboxylic acid, the primary and secondary hydroxyl groups, and the N-acetyl group (following deamidation). In some embodiments, compositions of HA in the present invention are provided that may be represent by Formula I, II, III and IV (FIG. 2).

Carboxylates in a HA backbond can be modified by carbodiimide-mediated reactions, esterification, and amidation. Hydroxyls in a HA backbond can be modified by etherify cation, divinylsulfone crosslinking, esterification, and bisepoxide crosslinking. Additionally, converting diols to aldehyde can be achieved through periodate oxidation of HA. Finally, deacetylation of the N-acetyl group of HA recovers an amino group which can then react with an acid using the same amidation.

The functional groups $R_1$, $R_2$, $R_3$, $R_4$ and $R_5$ comprise any one of or a combination of haloacetate, dihydrazide, amines, thiol, carboxylic acid, aldehyde, ketone, active hydrogen sites on aromatic ring, diene, azide isothiocyanates, isocyanates, acyl azides. N-hydroxysuccinimide (NHS) ester, sulfo-NHS, sulfonyl chloride, epoxides, carbonates, aryl halide, imidoesters, carbodiimides (e.g. N, N'-dicyclohexylcarbodiimide (DCC) and 1-ethyl-3-(3-dimethylaminopropyl) carbodiimide (EDC)), alkylphosphate compound, anhydride, fluorophenyl ester, hydroxymethyl phosphine, guanidino group, iodoacetyl derivative, maleimides, aziridines, acryloyl derivatives, arylating agents, disulfide derivative, vinylsulfone, phenylthioester, cisplatin, diazoacetate, carbonyl diimidazole, oxiranes, N, N'-disuccinimidyl carbonate, N-hydroxylsuccinimidyl chloroformate, alkyl halogens, hydrazine, maleimide, alkyne, and phosphorus-bound chlorine.

The telechelic polymers can be both synthetic polymers and natural polymers. Synthetic polymers comprise any one of or a combination of poly (aliphatic ester) (e.g. poly (lactide) (PLA), poly(ε-caprolactone) (PCL), poly(glycolic acid) (PGA), poly(lactic-co-glycolic acid) (PLGA), poly (trimethylene carbonate) (PTMC), polydioxanone (PDS), poly(ortho ester), polyanhydrides, poly(anhydride-co-imide), poly(anhydride-esters), polyurethanes (e.g. degrapols), poly(amide), poly(esteramide), poly(orthoesters), poly(dioxanones), poly(acetals), poly(ketals), poly (carbonate), poly(orthocarbonates), poly(hydroxylbutyrates), poly(hydroxyl-valerats), poly(alkylene oxalates), poly(alkylene succunates), poly(malic acid), poly(amino acids), poly(vinylpyrolidone), poly(hydroxycellulose), poly (glycerol sebacate), poly(ethylene imine), poly(acrylic acid) (PAA), poly(N,N'-diethylaminoethyl methacrylate, polyethylene glycol (PEG), poly(propylene oxide) (PPO), PEO-PPO block copolymers (e.g. pluronics (or poloxamers), and tetronic), poly(vinyl alcohol) (PVA), poly(N-isopropylacrylamide) (PNIPAm), Poly(N,N-diethylacrylamide) (PDEAAm), poly(oxazolines) (e.g. poly(2-methyloxazoline and poly(2-ethyl-2-oxazoline), oligo(ethylene glycol) fumarates (OPFs), poly(propylene fumarate), poly(alkyl cyanoacrylates), poly(acrylic amide), synthetic poly(amino acids) (e.g. poly (L-glutamic acid) (L-PGA) and poly (aspartic acid)), polyphosphazenes, poly(phosphoesters) and blends thereof.

The synthetic telechelic polymers can be prepared by conventional methods such as mass polymerization, solution (or homogeneous) polymerization, suspension polymerization, emulsion polymerization, radiation polymerization (using γ-ray, electron beam or the like). The synthetic telechelic polymers can be prepared by addition or chain growth polymerization, coordination polymerization, condensation or step growth polymerization. Addition or chain growth polymerization includes free radical polymerization, controlled-living radical polymerization (e.g. atom transfer radical polymerization (ATRP), reversible addition fragmentation transfer (RAFT) polymerization, and nitroxide-mediated radical polymerization (NMP)), cationic polymerizations, anionic polymerizations and the like.

The natural polymers comprise any one of or a combination of fibrin, collagen, matrigel, elastin, elastin-like peptides, albumin, natural poly (amino acids) (e.g. cyanophycin, poly (ε-1-lysine), poly (ʏ-glutamic acid)), polysaccharides (e.g. chitosan, dextran, chondroitin sulfate, agarose, alginate, methylcellulose and heparin), and blends thereof.

The conjugation of functional HA and telechelic polymers can be achieved by carbodiimide-mediated reactions, esterification, amidation, aldehyde and ketone reactions, active hydrogen reactions, photo-chemical reaction, azide-alkyne cycloaddition (e.g. copper-catalyzed azide-alkyne cycloaddition (CuAAC), copper-free azide-alkyne huisgen cycloaddition), thiol-click reaction, diels-alder reaction, nitrile oxide cycloaddition, and an enzymatic crosslinking strategy (e.g., horseradish peroxidase and hydrogen peroxide).

The conjugated linkages comprise any one of or a combination of isothiourea, isourea, amide, sulfonamide, shift-base, secondary amine, carbamate, arylamine, amidine, phosphoramidate, thioether, disulfide, β-thiosulfonyl, ester, carbamate, hydrazone, diazo, triazoles, carbohydrates, and amino acid esters bond.

Alternatively, a cross-linker HA-based polymer matrix can be produced via a 'grafting from' method (FIG. 1). A 'grafting from' method involves preparing the precursor to the backbone polymer with monomer units that contain functionalities ultimately capable of initiating polymerization of a second monomer [15]. In the embodiment, at least one of the monomeric units of HA is conjugated to at least one of polymerizable moiety, an initiator, an RAFT agent and an iniferter.

A polymerizable moiety includes any moiety that is capable of polymerizing upon exposure to a polymerizing initiator. A polymerizable moiety may include alkenyl moieties such as acrylates, methacrylates, dimethacrylates, oligoacrylates, oligomethoacrylates, ethacrylates, itaconates acrylamide, aldehydes, ethylenically unsaturated monomers. Ethylenically unsaturated monomers may include alkyl esters of acrylic or methacrylic acid, the nitrile and amides of the same acids, unsaturated monomers containing carboxylic acid groups, and polyethylenically unsaturated monomers. Examples of alkyl esters of acrylic or methacrylic acid are methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate. Examples of the nitrile and amides of the same acids are acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene, and butadiene. Examples of unsaturated monomers containing carboxylic acid groups include acrylic acid, methacrylic acid, ethacrylic acid, itaconic acid, maleic acid, fumaric acid, monoalkyl itaconate. Example of polyethylenically unsaturated monomers include butadiene, isoprene, allylmethacrylate, diacrylates of alkyl diols (e.g. butanediol diacrylate and hexanediol diacrylate, and divinyl benzene).

A RAFT agent moiety includes any moiety that is capable of trapping a propagating polymer radical and releasing a polymer fragment as a radical to achieve highly controlled polymerizations [16]. A RAFT agent moiety may include dithiobenzoates (e.g. cumyl dithiobenzoate, cyanopentanoic acid dithiobenzoate), trithiocarbonates (e.g. 4-cyano-4-(dodecylsulfanylthiocarbonyl) sulfanyl pentanoic acid, phthalimidylmethyl trithiocarbonates, S-1-dodecyl-S'-(α,α'-dimethyl-α"-acetic acid) trithiocarbonate (DATC), 3,5-bis(2-dodecylthiocarbonothioylthio-1-oxopropoxy) benzoic acid, 4-cyano-4-[(dodecylsulfanylthiocarbonyl)sulfanyl] pentanol, 4-cyano-4-[(dodecylsulfanylthiocarbonyl)sulfanyl] pentanoic acid), and xanthates.

An ATRP initiator moiety includes any moiety that is capable of initiating a polymerization during ATRP process [17]. Examples of an ATRP initiator moiety include, but not limited to, 2-bromopropanitrile (BPN), ethyl 2-bromoisobutyrate (BriB), ethyl 2-bromopropionate (EBrP), methyl 2-bromopropionate, 1-phenyl ethylbromide (1-PEBr), tosyl chloride (TsCl), 1-cyano-1-methylethyldiethyldithiocarbamte (MANDC), 2-(N,N-diethyldithiocarbamyl)-isobutyric acid ethyl ester (EMADC), and dimethyl 2,6-dibromoheptanedioate (DMDBHD).

An NMP iniferter includes, but not limited to, 2, 2, 6, 6-tetramethylpiperidinyloxy (TEMPO) and TEMPO based derivatives. TEMPO based derivatives includes, but not limited to, 4-acetamido-TEMPO, 4-acetamido-2,2,6,6-tetramethylpiperidine 1-oxyl purum, 4-amino-TEMPO, 2-azaadamantane-N-oxyl, 4-(2-bromoacetamido)-TEMPO, 4-carboxy-TEMPO, 4-cyano-TEMPO, 4-hydroxy-TEMPO purum, 4-hydroxy-TEMPO purum, 4-hydroxy-TEMPO benzoate, 4-(2-iodoacetamido)-TEMPO, 4-isothiocyanato-TEMPO, 4-maleimido-TEMPO, 4-methoxy-TEMPO, 4-oxo-TEMPO, 4-phosphonooxy-TEMPO hydrate, 2,2,6,6-tetramethyl-4-(methylsulfonyloxy)-1-piperidinooxy.

A polymerization reaction of the present invention can be conducted by conventional methods such as mass polymerization, solution polymerization, suspension polymerization, emulsion polymerization, radiation polymerization (using γ-ray, electron beam or the like), radical polymerization, controlled-living radical polymerization (e.g. ATRP, RAFT polymerization, and NMP), photopolymerization, ring-opening polymerization, and step-growth polymerization the like.

Polymerizing initiators include, but not limited to, electromechanical radiation, thermal initiators, redox initiators and photoinitiators. Initiation of polymerization may be accomplished by irradiation with light at a wavelength of between about 200 to about 700 nm. Redox-type initiators may be one or a combination of such initiators, tetramethylethylene, ferrous salt, sodium hydrogen sulfite or like reducing agent, etc. Examples of useful photoinitiators include 2, 2-dimethoxy-2-phenylacetophenone or a combination of ethyl eosin ($10^{-4}$ to $10^{-2}$ M) and triethanol amine (0.001 to 0.1 M). Examples of thermal initiators include, but not limited to, 4,4-azobis(4-cyanovaleric acid), benzoyl peroxide, azobisisobutyronitrile (AIBN), di-tertiary butyl peroxide and the like. Such systems would initiate free radical polymerization at physiological temperatures include, for example, potassium persulfate, with or without tetraamethyl ethylenediamine; benzoylperoxide, with or without triethanolamine; and ammonium persulfate with sodium bisulfite.

The HA-based drug delivery platform is developed from encapsulation of anesthetics, analgesics and antibiotics within a polymer matrix system through physical interactions or chemical interaction (e.g. polymer-drug conjugation).

Physical interactions comprise any one of or a combination of hydrophobic interaction, hydrophilic interaction, hydrogen bonding, and inter-molecular electrostatic interactions.

The polymer-therapeutic conjugation reactions comprise any one of or a combination of amine reaction, thiol reactions (e.g. thiol-ene click reactions, Michael addition), carboxylate reaction, hydroxyl reactions, aldehyde and ketone reactions, active hydrogen reactions, photo-chemical reaction, and cycloaddition reactions (e.g. diels-alder reaction, CuAAC, copper-free azide-alkyne huisgen cycloaddition).

The conjugated linkage comprise any one of or a combination of isothiourea, isourea, amide, sulfonamide, shift-base, secondary amine, carbamate, arylamine, amidine, phosphoramidate, thioether, disulfide, β-thiosulfonyl, ester, carbamate, hydrazone, diazo, 2+4 cycloaddition, 1, 2, 3-triazoles, carbohydrates, and amino acid esters bond.

EXAMPLES

Example 1

Materials

Hyaluronic acid sodium salt (HA) were purchased from Carbosynth Limited (Berkshire, UK). N-isopropylacrylamide (NIPAm) was purchased from Aldrich and was purified by recrystallization in hexane (3:1) before use. S-1-dodecyl-S'-(α,α'-dimethyl-α"-acetic acid) trithiocarbonate (DATC) was synthesized according to the related reference [18].

Example 2

Synthesis of HA-g-PNIPAm Via the Combination of Reversible Addition-Fragmentation Chain Transfer (RAFT) Polymerization and Thiol-Ene Click Reaction (FIG. 3).

The selection of a PNIPAm is based on its biocompatibility [19] and thermoresponsive phase transition characteristics that a hydrophilic coils-hydrophobic globules transition occurs around 32° C. [20, 21]. The combination of RAFT polymerization to fabricate well-defined molecular weight polymers with the efficient coupling mechanism of thiol-ene "click" chemistry allows highly controlled formation of HA hydrogels with distinct physical properties. The advantages of HA-g-PNIPAm are shown in FIG. 4.

(1) Synthesis of HA-ADH.

HA (100 mg) was dissolved in 20 mL of water to prepare an HA solution of 5 mg/mL. A 40 times molar excess of solid adipic acid dihydrazide (ADH) (1.736 g) was added to the solution and dissolved completely by mixing for 10 min. The pH of the mixed solution was adjusted to 4.8 by the addition of 1.0 N HCl. After that, four time molar excess of solid EDC (0.191 g) was added. The pH of the mixed solution was maintained at a value of 4.8 by the addition of 1.0 N HCl. The reaction was stopped by raising the pH of the reaction solution to 7.0 with 1.0 N NaOH. The reaction solution was dialyzed against a large excess amount of 100 mM NaCl solution, followed by dialysis against 25 vol % ethanol and deionized water using a dialysis membrane (MWCO, 12-14 kDa). The resulting solution was finally lyophilized for 3 days[13].

(2) Synthesis of HA-NAS.

100 mg HA-ADH was dissolved in 20 mL distilled water. N-acryloxysuccinimide (NAS) (0.5 g, 3 mmol) was subsequently added to the HA-ADH solution. The reaction continued with stirring at room temperature for 12 h. HA-NAS was dialyzed extensively against 100 m M NaCl solution, followed by dialysis against 25 vol % ethanol and deionized water using a dialysis membrane (MWCO, 12-14 kDa). The product was then lyophilized for 3 days to obtain solid acrylated HA (HA-NAS).

(3) Synthesis of Carboxyl Terminated PNIPAm by RAFT Polymerization.

The mixture of NIPAm (3.0 g, 94 mmol), DATC (0.1000 g, 0.35 mmol), AIBN (10.0 mg, 0.0625 mmol) and DMF (5.0 mL) was placed in a 10 mL polymerization tube. After oxygen was removed by purging argon, the sealed tube was immersed in a temperature controlled oil bath kept at 60° C. and stirred for 24 h. After the heating was stopped, the reaction mixture was dissolved with THF and then precipitated in 10-fold diethyl ether. The polymer was collected by filtration and dried in a vacuum oven at 40° C. [21].

(4) Aminolysis of PNIPAm.

The THF solution of PNIPAm and hexylamine was reacted for overnight at room temperature, the reaction mixture was precipitated from hexanes for three times and resulting aminolysis product, thiolated PNIPAm (PNIPAm-SH).

(5) Conjugation of HA-NAS with PNIPAm-SH Via a Thiol-Ene Click Reaction.

The PNIPAm-SH and HA-NAS was then solubilized in deionized (DI) water. After stirring for overnight, the resulting solution was purified by dialysis (MWCO 50 kDa) against DI water. The product (HA-g-PNIPAm) was then recovered by freeze-drying as a white powder. The chemical structures of products in each steps are confirmed by fourier transform infrared spectroscopy (FTIR) (FIG. 6) and $^1$H nuclear magnetic resonance (NMR) spectroscopy (FIG. 7). The NMR spectra were obtained on a Bruker ARX 400 MHz. $D_2O$ was used as a solvent for all the samples and the reported spectra represented an average of 64 scans.

Example 3

Synthesis of HA-g-PNIPAm Via a 'Grafting From' Method Using RAFT Polymerization (FIG. 4).

(1) Synthesis HA-Based Macro RAFT Agent.

To render hyaluronic acid soluble in DMSO, the sodium ions of HA were exchanged with the lipophilic tetrabutylammonium (TBA) ion. An aqueous solution (1 L) of HANa (10 mg/mL) was subjected to ion-exchange columnchromatography (Dowex 50w×8[H+], Dow Chemicals, Midland, Mich.) to obtain an aqueous solution (1.5 L) of HA [22]. Next, tetrabutylammonium bromide was added into 1000 mL of a 1% (w/w) HA solution in water and mixed for 2 h at room temperature. The mixture was then centrifuged for 2 min at 5000 rpm to remove the resin. The obtained HA-TBA solution was lyophilized. The success of synthesis of HA-TBA was confirmed by FTIR and $^1$H NMR. 1% (w/v) solution of HA-TBA in DMSO (100 mL) was prepared at 50° C. under a nitrogen atmosphere. Subsequently, 0.2 g of DMAP and a calculated amount of DATC and DCC, depending on the requested degree of substitution (DS), were added. The solution was stirred for 48 h at 50° C. HA-DATC was obtained by precipitation in diethyl ether for 3 times. The success of synthesis of HA-DATC was confirmed by UV-vis.

(2) Raft Polymerization.

The polymerization conditions for the synthesis of HA-g-PNIPAm nanocomposite are as follows: HA-DATC:AIBN:PNIPAm=1:0.2:500 and reaction mixture. In detail, a Schlenk flask was added with 80 mg of HA-DATC, 1 g of NIPAm, 2 mL of dry DMSO, and 0.55 mg of AIBN. The reaction mixture was degassed by four freezes-pump-thaw cycles and then was placed in a shaker at 70° C. After the reaction time, the polymerization was terminated by cooling via liquid nitrogen and the reaction mixtures were precipitated in 10-fold cold diethyl ether and were dried at 40° C. in vacuum. The conversion was determined gravimetrically.

Example 4

Hydrogel Formation and Gelation Time.

In brief, the HA-g-PNIPAm solutions (1-20 w/v %) at room temperature were quickly put in a water bath at 37° C. The time to form a gel (denoted as gelation time) is defined as the time when the gel, in an inverted state, shows no fluidity for 1 min [23]. The experiment was performed in triplicate. Table 1 indicates gelation temperature and gelation time of various concentration and molecular weight of HA-g-PNIPAm.

TABLE 1

Gelation temperature and time of HA-g-PNIPAm hydrogels.

| Samples | Gelation temperature (° C.) | Gelation time (S) |
|---|---|---|
| 15% HA-g-PNIPAm 13k | 32 | 30 |
| 15% HA-g-PNIPAm 5k | 29 | 30 |
| 10% HA-g-PNIPAm 13k | 32 | 90 |

Example 5

Rheological Characterization.

Rheological experiments were carried out with a new Discovery Series Hybrid Rheometer (DHR)-3 (TA) using parallel plate (20 mm diameter, 0° C.) configuration at 37° C. in the oscillatory mode. A 20 mm parallel plate geometry was used to perform strain sweeps and frequency sweeps at 37° C. Time sweep were performed to determine the gelation time of the hydrogel. Each hydrogel sample was used for only one test. Each test was performed in triplicate and the data represents the average of the three tests with corresponding standard deviation. The testing time to determine gelation time and modulus was very short and there was therefore no need to use a humidified chamber or trap for these experiments.

HA-g-PNIPAm is soluble in water at room temperature but rapidly forms a hydrogel at physiological temperature over a range of its concentration (5-15% w/v) as evidenced by an inverse method (FIG. 8 and FIG. 9). The hydrogel is able to retain its elasticity and shape when it is compressed (FIG. 10). Rheology testing (FIG. 11) showed that increase of the HA-g-PNIPAm concentration significantly increased the hydrogel stiffness. Accordingly, the elastic modulus of the 15% and 10% HA-g-PNIPAm hydrogels were ~42 kPa and ~32 kPa respectively indicating their highly elastic properties presumably due to double hydrogen bonding network within the hydrogel (FIG. 12).

Example 6

In Vitro Drug Release

In vitro morphine release was evaluated in a membrane based diffusion system. HA-g-PNIPAm with different concentrations (5-15% w/v) and morphine were prepared and loaded in a 3 mL syringe. The hydrogel were equilibrated for 10 min in a 37° C. incubator. The hydrogel was then dispensed into cell culture inserts (12 mm diameter with 3 μm pore size (Corning Incorporated, USA) in a 12 well plate. The hydrogels were then submerged with PBS and the well plate was placed into a 37° C. water bath. At specified time intervals, 1 mL of the solution from individual well was withdrawn and replaced with pre-heated water. Morphine concentration from the buffer solution was determined by UV spectrophotometry at 263 nm.

A sustained morphine release profile was observed in 48 hours due to diffusion of morphine from morphine-loaded HA-g-PNIPAm hydrogels (FIG. 13). Our hydrogel system also showed the feasibility to modulate the release profile simply via tuning the concentration of HA-g-PNIPAm concentration: after 48 hours, 15% HA-g-PNIPAM hydrogels had the slowest profile with ~70% cumulative release; 10% HA-g-PNIPAM hydrogels displayed an intermediate release profile with ~80% cumulative release. This result is consistent with the conclusion derived from the rheology data. In another in vitro study, the hydrogels supported cellular growth of both chondrocytes and bone marrow-derived stem cells with high viability during culture, implying that our hydrogels are cytocompatible.

Example 7

In Vivo Drug Release Through Subcutaneous Injections

In order to assess effectiveness of our hydrogel delivery system for analgesia, a conscious rat model that allows for quantification of morphine release in plasma along with the evaluation of biocompatibility of the hydrogels was employed. The specific protocols of in vivo efficacy assessment are designed as follows:

(1) Animal Population.

Rats (sample size n=10) were enrolled in the study. The study was randomized and blinded in pre-clinical trial. Each sprague dawley rat is assigned to 1 of 3 treatment groups including morphine-loaded hydrogels, positive control (morphine subcutaneous), negative controls (saline/hydrogel).

(2) Surgical Procedure.

Surgery under aseptic conditions was performed on individual rats. Isoflurane (3-5%) in anesthesia chamber was used for induction and maintenance with isoflurane (1.5-3%) with mask. Dorsal and ventral neck was shaved, scrubbed with Nolvasan, and swapped with alcohol. Both side of the flanks were shaved at 1×1 square shape. In our pilot study, pockets of hydrogels were visible after 3 days confirming hydrogel formation on subcutaneous injections of macromolecule solution through syringe and possibly allowing for a sustained release over a period of days (FIG. 14).

(3) Pharmacokinetic Study.

Blood samples were withdrawn from subcutaneous port at designed time points using carotid artery placement method in a conscious rat model after 24 hours post carotid artery catheterization. The decanted plasma subjected to SPE extraction. Additionally, a HPLC-mass spectrometry (HLPC-MS) method was identified for the reliable determination plasma level of morphine in rats. The analyte and internal standard (morphine-d3) were extracted from plasma samples by a single solid-phase extraction (SPE) method prior to HPLC-MS. Our standard calibration graph is linear within a range of 10-1000 ng/mL (r=0.999). In vivo drug release of morphine from HA-g-PNIPAm hydrogels was shown in FIG. 15. In vivo studies demonstrated HA-g-PNIPAm hydrogels enabled sustained release of morphine above the therapeutic plasma concentration (10 ng/mL) [24] up to 48 h (FIG. 15).

(4) Statistical Analysis.

Descriptive statistic and test of normality of data were done with Shapiro Wilk test. Depending on the normality of the data, either ANOVA will be employed (if data are normal) or Kruskal Wallis ANOVA statistical test will be utilized (if nonparametric) to compare between the treatment groups. Significance was set at $P<0.05$.

Example 8

In Vivo Drug Release Through Intra-Articular Injections

In vivo studies of the morphine-loaded novel hydrogels will be carried out in canine animal models to assert the validity of this system in pain-relief studies and the duration of analgesic effect in dogs and possibly man. Schematics of injectable hydrogels for intraarticular delivery of an analgesic or anesthetic was shown in FIG. 16. The specific protocols of in vivo efficacy assessment are designed as follows [25]:

(1) Animals.

Client-owned dogs with cranial cruciate ligament rupture will be enrolled in the study with owner informed consent.

(2) Experiment Design.

Study design is prospective, randomized and blinded clinical trial. A randomized number table will be used to assign dogs to 1 of 4 treatment groups for intra-articular administration of the following: saline solution (control group), morphine group (control group), hydrogel only (control group), and morphine loaded hydrogel (treatment group).

(3) Procedure.

Prior to surgery all dogs will be premedicated with hydromorphoine (0.1 mg/kg IM) and acepromazine (0.01 mg/kg IM) and anesthesia was induced with propofol (4-6 mg/kg, IM) and maintained with isoflurane (1-2.5% to effect) in 100% oxygen. Routine tibial tuberosity advancement (TTA) or tibial plateau leveling osteotomy (TPLO) through a medial skin and arthrotomy approach will be conducted by a board-certified veterinary surgeon or a surgical resident experienced in these techniques.

(4) Pain Assessment and Scoring.

All dogs will be assessed for signs of pain using modified criteria adopted from two pain scoring system, the dynamic and interactive visual analogue scale (DIVAS) for soft tissue surgery and the multifactorial pain score (MPS) developed for stifle arthrotomy study. The pain scoring assessment will be conducted at 2, 4, 6, 8, 10, 12, 16, 20, and 24 hours following the intra-articular injection by trained investigator, blinded to the intra-articular preparation used.

Rescue Parameter.

Dogs will be given rescue analgesia systemically if upon evaluation the score system exceed: 70 mm FOR DIVAS; Glascow Scale composite pain scale of 6.

Additional disclosure is found in Appendix-A, filed herewith, entirety of which is incorporated herein by reference into the present disclosure.

Those skilled in the art will recognize that numerous modifications can be made to the specific implementations described above. The implementations should not be limited to the particular limitations described. Other implementations may be possible. In addition, all references cited herein are indicative of the level of skill in the art and are hereby incorporated by reference in their entirety.

REFERENCES

[1] Uhrich K E, Cannizzaro S M, Langer R S, Shakesheff K M. Polymeric Systems for Controlled Drug Release. Chemical Reviews. 1999; 99:3181-98.

[2] Hoare T R, Kohane D S. Hydrogels in drug delivery: Progress and challenges. Polymer. 2008; 49:1993-2007.

[3] Bagshaw K R, Hanenbaum C L, Carbone E J, Lo K W, Laurencin C T, Walker J, et al. Pain management via local anesthetics and responsive hydrogels. Therapeutic delivery. 2015; 6:165-76.

[4] Calvert P. Hydrogels for Soft Machines. Advanced Materials. 2009; 21:743-56.

[5] Julian T, Yujie M, Bruekers S M C, Shaohua M, Huck W T S. 25th Anniversary Article: Designer Hydrogels for Cell Cultures: A Materials Selection Guide. Advanced Materials. 2014; 26:125-48.

[6] Lee K Y, Mooney D J. Hydrogels for tissue engineering. Chem Rev. 2001; 101:1869-79.

[7] Necas J, Bartosikova L, Brauner P, Kolar J. Hyaluronic acid (hyaluronan): a review. Veterinarni medicina. 2008; 53:397-411.

[8] Burdick J A, Prestwich G D. Hyaluronic Acid Hydrogels for Biomedical Applications. Advanced Materials. 2011; 23:H41-H56.

[9] Thiele J, Ma Y, Bruekers S M C, Ma S, Huck W T S. 25th Anniversary Article: Designer Hydrogels for Cell Cultures: A Materials Selection Guide. Advanced Materials. 2014; 26:125-48.

[10] Bhatia D, Bejarano T, Novo M. Current interventions in the management of knee osteoarthritis. Journal of Pharmacy & Bioallied Sciences. 2013; 5:30-8.

[11] Moskowitz R W. Osteoarthritis: diagnosis and medical/surgical management: Lippincott Williams & Wilkins; 2007.

[12] Mero A, Campisi M. Hyaluronic acid bioconjugates for the delivery of bioactive molecules. Polymers. 2014; 6:346-69.

[13] Kirker K R, Luo Y, Nielson J H, Shelby J, Prestwich G D. Glycosaminoglycan hydrogel films as bio-interactive dressings for wound healing. Biomaterials. 2002; 23:3661-71.

[14] Hu X, Li D, Zhou F, Gao C. Biological hydrogel synthesized from hyaluronic acid, gelatin and chondroitin sulfate by click chemistry. Acta Biomaterialia. 2011; 7:1618-26.

[15] Grigoriadis C, Nese A, Matyjaszewski K, Pakula T, Butt H-J, Floudas G. Dynamic Homogeneity by Architectural Design—Bottlebrush Polymers. Macromolecular Chemistry and Physics. 2012; 213:1311-20.

[16] Motokucho S, Sudo A, Endo T. Polymer having a trithiocarbonate moiety in the main chain: Application to reversible addition-fragmentation chain transfer controlled thermal and photoinduced monomer insertion polymerizations. Journal of Polymer Science Part A: Polymer Chemistry. 2006; 44:6324-31.

[17] Matyjaszewski K. Atom Transfer Radical Polymerization (ATRP): Current Status and Future Perspectives. Macromolecules. 2012; 45:4015-39.

[18] Lai J T, Filla D, Shea R. Functional polymers from novel carboxyl-terminated trithiocarbonates as highly efficient RAFT agents. Macromolecules. 2002; 35:6754-6.

[19] Cooperstein M A, Canavan H E. Assessment of cytotoxicity of (N-isopropyl acrylamide) and Poly (N-isopropyl acrylamide)-coated surfaces. Biointerphases. 2013; 8:19.

[20] Eeckman F, Moës A J, Amighi K. Synthesis and characterization of thermosensitive copolymers for oral controlled drug delivery. European Polymer Journal. 2004; 40:873-81.

[21] Hua D, Jiang J, Kuang L, Jiang J, Zheng W, Liang H. Smart Chitosan-Based Stimuli-Responsive Nanocarriers for the Controlled Delivery of Hydrophobic Pharmaceuticals. Macromolecules. 2011; 44:1298-302.

[22] Ohya S, Nakayama Y, Matsuda T. Thermoresponsive artificial extracellular matrix for tissue engineering: hyaluronic acid bioconjugated with poly (N-isopropylacrylamide) grafts. Biomacromolecules. 2001; 2:856-63.

[23] Cal S, Liu Y, Shu X Z, Prestwich G D. Injectable glycosaminoglycan hydrogels for controlled release of human basic fibroblast growth factor. Biomaterials. 2005; 26:6054-67.

[24] Linares O A, Linares A L. Computational Opioid Prescribing: A Novel Application of Clinical Pharmacokinetics. Journal of Pain & Palliative Care Pharmacotherapy. 2011; 25:125-35.

[25] Soto N, Fauber A E, Ko J C, Moore G E, Lambrechts N E. Analgesic effect of intra-articularly administered morphine, dexmedetomidine, or a morphine-dexmedetomidine combination immediately following stifle joint surgery in dogs. Journal of the American Veterinary Medical Association. 2014; 244:1291-7.

The invention claimed is:

1. A composition comprising a polymer matrix comprising:

a functionalized hyaluronic acid (HA) of at least 100 monomeric units, each unit comprising a first functional amino group with a theoretical degree of substitution ranging from 20% to 80% per monomeric unit of HA resulting in at least one unreacted amino group and a second functional group comprising a polymerizable moiety comprising an acrylate moiety; and a telechelic polymer comprising a functional group reactive toward said second functional group of the HA, wherein:

said functionalized HA and said telechelic polymer are linked by a covalent bond formed between said second functional group of HA and the telechelic polymer, gelation of said polymer matrix is reversible due to the presence of intra- and intermolecular hydrogen bonds between isopropyl groups and the at least one unreacted amino groups of the polymer matrix, and the telechelic polymer is thiolated poly (N-isopropylacrylamide) (PNIPAm).

2. The composition according to claim 1, wherein the functionalized HA comprises formula I, II, or IV:

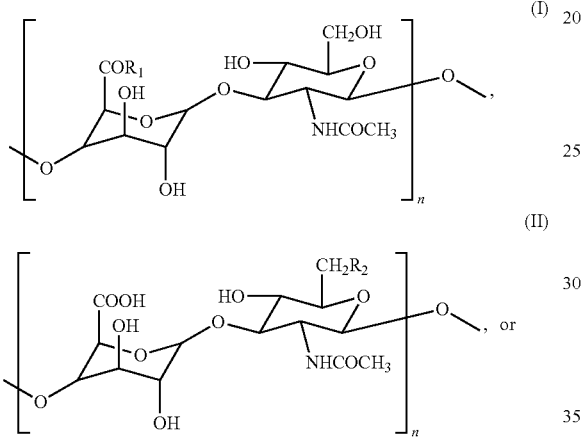

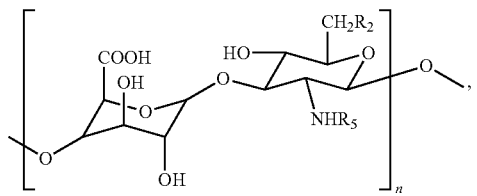

wherein $R_1$, $R_2$, and $R_5$ each independently comprises any one of or a combination of haloacetates, hydrazides, amines, thiols, carboxylic acids, aldehydes, ketones, dienes, azide isothiocyanates, isocyanates, acyl azides, N-hydroxysuccinimide (NHS) esters, sulfo-NHS, sulfonyl chloride, epoxides, carbonates, aryl halides, imidoesters, carbodiimides, alkylphosphate compounds, anhydrides, fluorophenyl esters, hydroxymethyl phosphines, iodoacetyl derivatives, maleimides, aziridines, acryloyl derivatives, disulfide derivatives, vinylsulfone, phenylthioester, diazoacetates, carbonyl diimidazoles, oxiranes, N, N'-disuccinimidyl carbonates, N-hydroxylsuccinimidyl chloroformates, alkyl halogens, hydrazines, alkynes, and phosphorus-bound chlorine.

3. The composition of claim 1, wherein the polymerizable moiety of the functionalized HA comprises a methyl acrylate moiety.

4. The composition of claim 1, wherein a theoretical substitution degree of the second functional group of the duly functionalized HA ranges from 20% to 79% per monomeric unit of HA.

5. The composition of claim 1, wherein the telechelic polymer comprises a thiol group at an end of each main chain of the PNIPAm and has a molecular weight ranging from 5 to 20 kDa.

* * * * *